US009695444B2

(12) United States Patent
Fukumura et al.

(10) Patent No.: US 9,695,444 B2
(45) Date of Patent: *Jul. 4, 2017

(54) VACCINE PREPARED UTILIZING HUMAN PARAINFLUENZA VIRUS TYPE 2 VECTOR

(71) Applicants: BioComo, Inc., Mie (JP); Mie University, Mie (JP)

(72) Inventors: Masayuki Fukumura, Mie (JP); Junpei Ohtsuka, Mie (JP); Tetsuya Nosaka, Mie (JP); Masato Tsurudome, Mie (JP); Mitsuo Kawano, Mie (JP); Ken-ichiro Hara, Mie (JP)

(73) Assignees: BIOCOMO INC., Mie (JP); MIE UNIVERSITY, Mie (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/655,417

(22) PCT Filed: Dec. 25, 2013

(86) PCT No.: PCT/JP2013/007598
§ 371 (c)(1),
(2) Date: Jun. 25, 2015

(87) PCT Pub. No.: WO2014/103310
PCT Pub. Date: Jul. 3, 2014

(65) Prior Publication Data
US 2015/0329874 A1 Nov. 19, 2015

(30) Foreign Application Priority Data
Dec. 26, 2012 (JP) .................. 2012-283421

(51) Int. Cl.
| | | |
|---|---|---|
| *C12N 15/00* | (2006.01) | |
| *C12N 15/86* | (2006.01) | |
| *C12N 7/00* | (2006.01) | |
| *A61K 39/00* | (2006.01) | |
| *A61K 39/145* | (2006.01) | |
| *C12N 15/09* | (2006.01) | |
| *A61K 39/12* | (2006.01) | |
| *A61K 39/155* | (2006.01) | |

(52) U.S. Cl.
CPC .......... *C12N 15/86* (2013.01); *A61K 39/0011* (2013.01); *A61K 39/12* (2013.01); *A61K 39/145* (2013.01); *A61K 39/155* (2013.01); *C12N 7/00* (2013.01); *C12N 15/09* (2013.01); *A61K 2039/5252* (2013.01); *A61K 2039/5256* (2013.01); *C07K 2319/00* (2013.01); *C12N 2760/16034* (2013.01); *C12N 2760/18734* (2013.01); *C12N 2760/18743* (2013.01); *C12N 2760/18762* (2013.01); *C12N 2760/18763* (2013.01)

(58) Field of Classification Search
None
See application file for complete search history.

(56) References Cited

U.S. PATENT DOCUMENTS

| | | | | |
|---|---|---|---|---|
| 7,226,786 | B2* | 6/2007 | Kitazato | ............... A61K 48/00 435/455 |
| 8,911,975 | B2* | 12/2014 | Fukumura | ............... C12N 7/00 435/235.1 |
| 2002/0169306 | A1 | 11/2002 | Kitazato et al. | |
| 2003/0170266 | A1 | 9/2003 | Kitazato et al. | |
| 2005/0142148 | A1 | 6/2005 | Fouchier et al. | |
| 2005/0221292 | A1 | 10/2005 | Kinoh et al. | |
| 2014/0322760 | A1 | 10/2014 | Fukumura et al. | |

FOREIGN PATENT DOCUMENTS

| | | |
|---|---|---|
| CN | 101054419 A | 10/2007 |
| EP | 1505154 A1 | 2/2005 |
| JP | 2004329222 A | 11/2004 |
| JP | 2006512904 A | 4/2006 |
| JP | 2006524511 A | 11/2006 |
| WO | 0103744 A2 | 1/2001 |
| WO | 03029416 A2 | 4/2003 |
| WO | 2004027037 A2 | 4/2004 |
| WO | 2008061243 A2 | 5/2008 |
| WO | 2012108195 A1 | 8/2012 |

OTHER PUBLICATIONS

Zimmer et al. J Virol 2005;79:10467-10477.*
King, Avian Dis 1991;35:505-14.*
Hikono et al. Vet Immunol Immunopathol 2012;146:92-96.*
Yang, et al., A paramyxovirus-vectored intranasal vaccine against Ebola virus is immunogenic in vector-immune animals; Virology, vol. 377, 2008, pp. 255-264.
Tompkins, et al., Recombinant parainfluenza virus 5 (PIV5) expressing the influenza A virus hemagglutinin provides immunity in mice to influenza A virus challenge; Virology, vol. 362, 2007, pp. 139-150.
Vigil et al., Recombinant Newcastle Disease Virus as a Vaccine Vector for Cancer Therapy; Molecular Therapy, vol. 16, No. 11, 2008, pp. 1883-1890.
Kortekaas, et al., Intramuscular inoculation of calves with an experimental Newcastle disease virus-based vector vaccine elicits neutralizing antibodies against Rift Valley fever virus; Vaccine, vol. 28, 2010, pp. 2271-2276.

(Continued)

*Primary Examiner* — Janice Li
(74) *Attorney, Agent, or Firm* — Pearne & Gordon LLP

(57) ABSTRACT

Disclosed are: a virus vector in which a gene encoding an antigenic polypeptide is integrated in human parainfluenza virus type 2 gene, wherein the antigenic polypeptide is expressed in the form of a fusion protein with a viral structural protein; and a method for producing the same. The virus vector of the present invention contains a quantitatively large amount of the antigenic peptide on the virus particle and can efficiently deliver the antigenic polypeptide to a target cell.

16 Claims, 14 Drawing Sheets

(56) References Cited

OTHER PUBLICATIONS

Kumar, et al., Evaluation of the Newcastle Disease Virus F and HN Proteins in Protective Immunity by Using a Recombinant Avian Paramyxovirus Type 3 Vector in Chickens, Journal of Virology, vol. 85, No. 13, Jul. 2011, pp. 6521-6534.

Schmidt, et al., Mucosal Immunization of Rhesus Monkeys against Respiratory Syncytial Virus Subgroups A and B and Human Parainfluenza Virus Type 3 by Using a Live cDNA-Derived Vaccine Based on a Host Range-Attenuated Bovine Parainfluenza Virus Type 3 Vector Backbone; Journal of Virology, vol. 76, No. 3, 2002, pp. 1089-1099.

Moriya, et al., Intranasal Sendai viral vector vaccination is more immunogenic than intramuscular under pre-existing anti-vector antibodies; Vaccine, vol. 29, 2011, pp. 8557-8563.

Carnero, et al., Optimization of Human Immunodeficiency Virus Gag Expression by Newcastle Disease Virus Vectors for the Induction of Potent Immune Responses; Journal of Virology, vol. 83, No. 2, Jan. 2009, pp. 584-597.

Hikono, et al., Induction of a cross-reactive antibody response to influenza virus M2 antigen in pigs by using Sendai virus vector; Veterinary Immunology and Immunopathology, vol. 146, 2012, pp. 92-96.

International Search Report for PCT/JP2013/007598, mailed Mar. 18, 2014.

Extended European Search Report dated Jul. 12, 2016 for EP 13868750.4.

Tao T et al., "Recovery of a Fully Viable Chimeric Human Parainfluenza Virus (PIV) Type 3 in Which the Hemagglutinin Neuraminidase and Fusion Glycoproteins Have Been Replaced by Those of PIV Type 1," Journal of Virology, vol. 4, No. 72, pp. 2955-2961, Apr. 1, 1998.

Harrison M.S. et al., "Paramyxovirus assembly and budding: Building particles that transmit infections," The International Journal of Biochemistry & Cell Biology, vol. 42, No. 9, pp. 1416-1429, Sep. 1, 2010.

Ohtsuka J. et al., "Vero/BC-F: an efficient packaging cell line stably expressing F Protein to generate single round-infectious human parainfluenza virus type 2 vector," Gene Therapy, vol. 21, No. 8, pp. 775-784, Jun. 19, 2014.

Tsurudome, Masato, "Virus Entry: Parainfluenza Viruses," in "Negative Strand RNA Virus" (ed. Luo, Ming), The University of Alabama at Birmingham, USA. 2011, cover page, copyright page, table of contents page, and pp. 35-61.

Ohtsuka, J., et al. "Vero/BC-F: an efficient packaging cell line stably expressing F protein to generate single round-infectious human parainfluenza virus type 2 vector." Gene Therapy advance online publication (Jun. 19, 2014) doi: 10.1038/gt.2014.55, pp. 1-10.

Chinese Office action issued in corresponding Chinese Patent Application No. 201380068169.4 dated Jan. 25, 2017, 6 pages.

* cited by examiner

Fig. 9

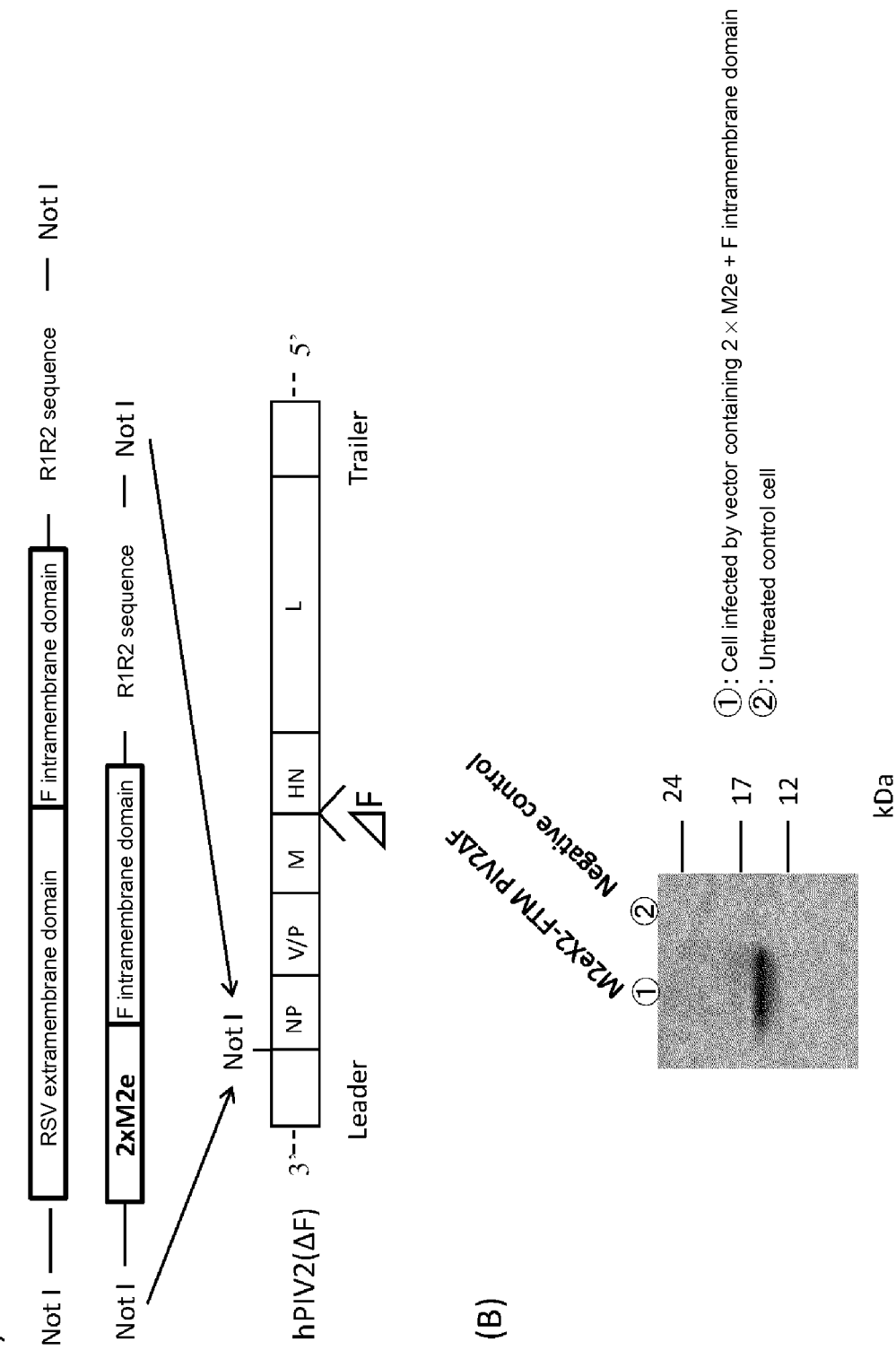

VACCINE PREPARED UTILIZING HUMAN PARAINFLUENZA VIRUS TYPE 2 VECTOR

TECHNICAL FIELD

The present invention relates to an RNA virus vector useful as a vaccine for prevention or treatment of a disease and an inactivated vaccine.

BACKGROUND ART

Viruses of the family Paramyxoviridae have negative-sense single-stranded RNA as the genome. Their vectors capable of highly expressing a foreign gene have been prepared by reverse genetics methods and considered to have excellent properties as vectors for gene therapy or vectors for recombinant vaccines. The life cycles of these viruses are free from DNA phase. In addition, all processes of transcription and replication occur cytoplasmically outside the nucleus. For these reasons, the probability of homologous recombination with chromosomal DNA is very small, and the risk of developing cancer due to gene recombination into the chromosome is also small.

The present inventors have previously attempted to vectorize human parainfluenza virus type 2 (hereinafter, referred to as hPIV2), a negative-sense single-stranded RNA virus, belonging to the genus *Rubulavirus* within the subfamily Paramyxovirinae of the family Paramyxoviridae, and studied use thereof as vectors for vaccines and for gene therapy.

In this process, the present inventors have constructed an F gene-defective vector of hPIV2 completely lacking the F gene of a viral structural protein. This vector has non-transmissible or single-round-infectious properties. The present inventors have also successfully obtained stably F gene-expressing packaging cells having the ability to produce high-titer vectors for production of the F gene-defective vector. The F gene-defective vector can yield an infectious vector carrying the F protein on the virus envelope, only in packaging cells expressing F gene. On the other hand, in cells or tissues expression of F gene, this vector can do so-called self-replication, but cannot yield an infectious vector. Inexhaustible vector multiplication therefore does not occur in recipients. Thus, this vector is highly safe (Patent Literature 1).

Nonclinical trials, clinical research, clinical trials, etc., have reported many results indicating the efficacy of vaccines or gene therapy using recombinant live RNA virus vectors or attenuated recombinant RNA viruses (Non Patent Literatures 1 to 9). At the moment, however, there is no report on recombinant live RNA virus vector preparations approved as medicines by the Food and Drug Administration and the European Medicines Agency. This is presumably because in the case of using recombinant live RNA viruses as vectors, large amounts of viruses and foreign gene products are still produced in infected cells, though safety measures are taken in such a way that pathogenicity is reduced by use of attenuated viruses or non-transmissible vectors are utilized; thus concerns such as their influence on homeostasis or mutations of the foreign genes cannot be dispelled.

Thus, vaccines whose genome has been inactivated or degraded into components so as to prevent the transcription or replication of the virus are highly safe. Treatment methods with formalin are often used in the preparation of such inactivated vaccines.

Unfortunately, the inactivated vaccines, which are considered to be highly safe, also present safety problems. In the 1960s, a formalin-inactivated RSV vaccine was developed from RSV belonging to the family Paramyxoviridae, and vaccination with this vaccine resulted in severe infant patients and two cases of death after the natural infection of RSV. Then, the cause thereof was intensively investigated. The inactivation treatment of the virus with formalin was found to alter the three-dimensional structure of F membrane protein. It was revealed that antibodies having no neutralizing activity against the F membrane protein altered by the vaccination are produced, and the antibody having neutralizing activity against the F membrane protein having a normal structure is not produced because the F membrane protein having a normal structure is absent due to the formalin treatment. After the vaccination, the natural infection of the RSV virus causes the response of the body to excessively produce the antibodies having no neutralizing activity in order to suppress the multiplication of the virus. As a result, a large number of eosinophils, which are not seen in common RSV infection, are infiltrated into lung tissues. Along with this, the levels of cytokines such as IL-4 and IL-5 are elevated so that neither local IgA antibodies nor cellular immunity is induced, probably leading to increased severity.

In addition, the formalin-inactivated RSV is known to be inferior in the ability to maturate dendritic cells, which are antigen-presenting cells, to live RSV. Inactivation by UV treatment, heat treatment, or the like, without the use of formalin has also been studied, but has not yet been put in practical use because all of these treatments have the low ability to activate dendritic cells and further induce inflammatory response. Likewise, the infiltration of eosinophils and atypical measles have also been reported as to a formalin-inactivated vaccine of measles virus belonging to the family Paramyxoviridae.

Meanwhile, animal testing has reported that an inactivated RSV vaccine designed to be able to induce Th1 immunity is effective for preventing viral infection. This suggests the possibility that an inactivated vaccine that can induce Th1 can solve these problems.

Virus vectors are considered to offer high in vivo transgene expression. Some reports, however, show that these vectors are not highly workable as vectors for gene therapy, because the transgene expression in virus-infected cells or tissues is not quantitative or has a low expression level. The suppression of expression by pre-existing antibodies against the transferred virus vectors or the suppression of expression by antibodies against the virus vectors associated with a plurality of doses of the vectors has also been reported. These reports imply the difficulty in using virus vectors having the high ability to induce antibodies, in gene therapy, which requires over a certain level of gene expression, albeit transient.

In the case of transferring a foreign gene to a virus vector and expressing the gene, the foreign gene product has no packaging signal and, therefore, is usually not contained in the vector. The virus vector after in vivo administration infects a recipient cell where transcription and replication in turn occur so that the foreign gene product is produced for the first time. Thus, the expression of the foreign gene is suppressed or reduced when neutralizing antibodies or the like inhibit the infection, transcription or replication, etc., of the virus vector.

The efficiency of viral infection of cells or tissues is low in vivo, or even if the cells or tissues are virus-infected, transcription or replication does not occur or occurs with very poor efficiency in vivo so that the foreign gene is hardly expressed in most cases. This is probably because, for example: in in vivo infected cells, interferons or the like induced by the viral infection minimize the transcription or replication of the virus; and extracellular matrix or the like hinders the virus vector from reaching a target cell.

CITATION LIST

Patent Literature

Patent Literature 1: WO2012/108195

Non Patent Literature

Non Patent Literature 1: Virology. 377 (2), 255, (2008)
Non Patent Literature 2: Virology. 362 (1), 139, (2007)
Non Patent Literature 3: Molecular Therapy. 16 (11), 1883 (2008)
Non Patent Literature 4: Vaccine. 28, 2271, (2010)
Non Patent Literature 5: J Virol. 6521, (2011)
Non Patent Literature 6: J Virol. 1089, (2002)
Non Patent Literature 7: Vaccine. 29, 8557, (2011)
Non Patent Literature 8: J Virol. 584, (2009)
Non Patent Literature 9: Vet Immunol Immunopathol. 146 (1), 92, (2012)

SUMMARY OF INVENTION

Technical Problem

An object of the present invention is to provide a virus vector of the family Paramyxoviridae that is useful as a vaccine for prevention or treatment of a disease and is capable of efficiently delivering an antigenic polypeptide (including an antigenic protein and peptide) to a target cell, and an inactivated vector.

Solution to Problem

The present inventors have found that an antigenic protein or peptide can be delivered efficiently and quantitatively to a target cell by fusing a structural gene of a virus with a gene of the antigenic protein or peptide, followed by expression.

The present inventors have also successfully constructed the following 4 types of vectors: 1) a type in which an antigen gene is located on the 3'-terminal side (hereinafter, concerning a coding strand) of a gene of membrane protein HN, whereby the antigenic peptide is expressed outside the vector envelope; 2) a type in which an antigen gene is located on the 3'-terminal side of F gene of an F-packaging cell, whereby the antigenic peptide is expressed inside the vector envelope; 3) a type of 1) and 2) in combination, whereby the antigenic peptide is expressed both inside and outside the vector envelope; and 4) a type in which an antigen is fused with a membrane or intracellular domain of a membrane protein functioning as a viral packaging signal, whereby the antigen is taken up on the vector. This allows a plurality of antigens to be transferred in various manners to vectors.

Specifically, the present invention relates to a virus vector capable of efficiently delivering an antigenic polypeptide to a target cell and specifically provides the following aspects:
[1] a virus vector in which a gene encoding an antigenic polypeptide is integrated in a viral gene of the family Paramyxoviridae, wherein the antigenic polypeptide is expressed in the form of a fusion protein with a viral structural protein or a portion thereof;
[2] the virus vector according to [1], wherein the fusion protein is a fusion protein with one or more selected from HN protein, F protein, and M protein of the virus, or a portion thereof;
[3] the virus vector according to [1] or [2], wherein the gene encoding an antigenic polypeptide is
1) located on the 3'-terminal side of the HN gene, wherein the antigenic polypeptide is expressed outside the vector envelope,
2) located on the 3'-terminal side of the F gene, wherein the antigenic polypeptide is expressed inside the vector envelope, or
3) located on each of the 3'-terminal side of the HN gene and the 3'-terminal side of the F gene, wherein the antigenic polypeptide is expressed both outside and inside the vector envelope;
[4] the virus vector according to [1] or [2], wherein the antigenic polypeptide is fused with a membrane or intracellular domain of the F or HN membrane protein serving as a viral packaging signal so that the antigenic polypeptide is retained on the vector envelope;
[5] the virus vector according to any of [1] to [4], wherein the virus is an F protein-defective virus of the family Paramyxoviridae;
[6] the virus vector according to any of [1] to [5], wherein the virus has undergone nucleic acid inactivation treatment;
[7] the virus vector according to [6], wherein the nucleic acid inactivation treatment avoids altering (does not substantially alter) the structure of the virus envelope;
[8] the virus vector according to any of [1] to [7], wherein the antigenic polypeptide is influenza virus M2e protein or a fragment thereof;
[9] the virus vector according to any of [1] to [7], wherein the antigenic polypeptide is any one or more selected from: the group consisting of an antigenic peptide of a virus selected from influenza viruses including a highly virulent influenza virus, parainfluenza virus type 3, RS virus, Hendra virus, SARS virus, Nipah virus, Lassa virus, dengue virus, West Nile virus, human metapneumovirus, Ebola virus, hantavirus, AIDS virus, hepatitis C virus, Lassa virus, human papillomavirus, rubella virus, rotavirus, norovirus, Crimean-Congo hemorrhagic fever virus, herpesvirus, cytomegalovirus, and papillomavirus; the group consisting of an antigenic peptide of a bacterium selected from A beta-hemolytic *streptococcus, Mycobacterium tuberculosis, Vibrio cholerae*, and *mycoplasma*; and the group consisting of an antigen selected from RSV F protein, cancer antigens gp100, MUC1, NY-ESO-1, MelanA/MART1, TRP2, MAGE, CEA, CA125, HER2/neu, WT1, and PSA; or fragment(s) thereof;
[10] a method for producing a virus vector of the family Paramyxoviridae by which an antigenic polypeptide is expressed in the form of a fusion protein with a viral structural protein or a portion thereof, the method comprising the steps of: coculturing, with Vero cells, a virus of the family Paramyxoviridae in which a gene encoding the fusion protein is integrated in a viral gene; and isolating virus particles from the culture supernatant;
[11] the method according to [10], wherein the fusion protein is a fusion protein with one or more selected from HN protein, F protein, and M protein of the virus, or a portion thereof;
[12] the method according to [10] or [11], wherein the fusion protein is a fusion protein with an intracellular domain of the HN protein or the F protein of the virus;

[13] the method according to any of [10] to [12], wherein the antigenic polypeptide is
1) fused on the C-terminal side of the HN protein and expressed outside the vector envelope,
2) fused on the N- or C-terminal side of the F protein or on the N-terminal side of the HN protein and expressed inside the vector envelope, or
3) fused on each of the C-terminal side of the HN protein and the N- or C-terminal side of the F protein or the N-terminal side of the HN protein and expressed both outside and inside the vector envelope;
[14] the method according to any of [10] to [12], wherein the antigenic polypeptide is fused with a membrane or intracellular domain of the HN protein or the F protein of the virus so that the antigenic polypeptide is included on the vector envelope;
[15] the method according to any of [10] to [14], wherein the method comprises: coculturing an F gene-defective virus of the family Paramyxoviridae with Vero cells expressing the F gene of the virus of the family Paramyxoviridae or the F gene fused with the antigen; and isolating virus particles from the culture supernatant;
[16] the method according to any of [10] to [15], further comprising the step of subjecting the virus to nucleic acid inactivation treatment;
[17] the method according to [16], wherein the nucleic acid inactivation treatment avoids altering (does not substantially alter) the structure of the virus envelope;
[18] the method according to any of [10] to [17], wherein the antigenic polypeptide is influenza virus M2e protein or a fragment thereof;
[19] the method according to any of [10] to [18], wherein the antigenic polypeptide is any one or more selected from: the group consisting of an antigenic peptide of a virus selected from influenza viruses including a highly virulent influenza virus, parainfluenza virus type 3, RS virus, Hendra virus, SARS virus, Nipah virus, Lassa virus, dengue virus, West Nile virus, human metapneumovirus, Ebola virus, hantavirus, AIDS virus, hepatitis C virus, Lassa virus, human papillomavirus, rubella virus, rotavirus, norovirus, Crimean-Congo hemorrhagic fever virus, herpesvirus, cytomegalovirus, and papillomavirus; the group consisting of an antigenic peptide of a bacterium selected from group A beta-hemolytic *streptococcus, Mycobacterium tuberculosis, Vibrio cholerae, mycoplasma*; and the group consisting of RSV F protein; cancer antigens gp100, MUC1, NY-ESO-1, MelanA/MART1, TRP2, MAGE, CEA, CA125, HER2/neu, WT1, and PSA, or fragment(s) thereof; and
[20] a Vero cell comprising antigen gene-fused F gene of a virus of the family Paramyxoviridae and expressing a fusion protein between the antigen and the F protein.

Advantageous Effects of Invention

1) The problem of the conventional platform-type inactivated virus vector is that the amount of an antigen transferred per vector is low; thus, antibody production efficiency is low. By contrast, the virus vector of the present invention can contain a quantitatively large amount of an antigenic peptide on the virus particle.
2) According to the present invention, the fused structural protein, particularly, the fused membrane protein, from the virus vector has immunogenicity in itself. High immunity can therefore be induced against the low immunogenic antigenic polypeptide fused with this protein. Specifically, the vector itself has adjuvant activity and thus eliminates the need of adding an adjuvant or reduces the amount of an adjuvant added for administration.
3) The virus vector of the present invention transfers an antigen and an adjuvant to the same cell and can thus reduce the inefficient induction of immunity attributed to the uptake of a peptide and an adjuvant administered as a mixture into different cells.
4) The human parainfluenza virus used in the present invention is a negative-sense single-stranded virus terminally modified with triphosphate (5'-PPP). A single-stranded RNA moiety having this terminal triphosphate and following several bases serves as a substrate for an intracellular signal called IFIT. Thus, this moiety induces type 1 interferon or the like having antivirus activity and contributes to DC cell maturation, etc. (Abbas Y T., Nature, Vol. 494, Issue 7435, pp. 60-64 (2013); and Saito T. et al., J. Exp. Med. Vol. 205, No. 7, pp. 1523-1527 (2008)).
5) According to the present invention, nucleic acid inactivation is carried out using a low concentration of β-propiolactone or the like. The three-dimensional structures of virus envelope proteins are therefore maintained, while only the virus genome is inactivated with the functions of these proteins maintained. Hence, the vector has cell adsorption properties similar to those of live viruses and can exert the ability to induce immunity and the ability to mature DC cells by virtue of the aforementioned structures.
6) From these advantages, the virus vector of the present invention can be expected to have high effects even on humans, unlike the conventional virus vector, which cannot be expected to produce sufficient effects.
7) The transfer of an antigen at the gene level eliminates the need of transferring the antigen after inactivation and can circumvent problems associated with the transfer of the antigen after inactivation (low antigen transfer efficiency, disruption of an envelope structure, etc.).
8) The virus vector of the present invention can be constituted such that the antigen can be located outside or inside, or both outside and inside the vector envelope. This allows a plurality of antigens to be transferred in various manners to vectors.

As described above, according to the present invention, an inactivated vector capable of inducing immunity comparable to live virus vectors for dendritic cells or the like can be obtained by efficient virus inactivation treatment. Thus, an opportunity can be opened up for the development of an inactivated vector vaccine using a virus of the family Paramyxoviridae.

BRIEF DESCRIPTION OF DRAWINGS

FIG. 6(A) shows the GFP fluorescence of vectors at Day 5 and Day 10.
FIG. 6(B) shows hemagglutination reaction (HA titer).
FIGS. 6(C) to 6(E) each show antibody levels (IgG1, IgG2, and IgA) in alveolar lavages after administration of live hPIV2/ΔF/GFP, β-propiolactone-treated hPIV2/ΔF/GFP, and formalin-treated hPIV2/ΔF/GFP.

FIG. 8(A) is a diagram showing the genome of hPIV2(ΔF) for an antigen fused with HN (fused antigen: e.g., M2e peptide, gp-100 peptide, or WT-1 peptide). FIG. 8(B) is a schematic diagram of inactivated hPIV2 (ΔF) for an antigen fused with HN. FIG. 8(C) shows results of confirming the antigen from an antigen transfer virus for HN by Western blot (HN-M2e represents the antigen transfer virus, and HN represents an antigen transfer-free virus; anti-M2 antibody-positive reaction was observed only for HN-M2e).

FIG. 9(A) is a diagram showing a plasmid vector for packaging cell establishment for producing a fusion protein among hPIV2, F protein in a packaging cell, and an antigen (fused antigen: e.g., M2e peptide, gp-100 peptide, or WT-1 peptide). FIG. 9(B) shows results of antigen transfer of a recovered vector by Western blot. The Western blot images depict hPIV2 wt: an antigen transfer-free virus, HN-M2e hPIV2ΔF: an antigen transfer virus for HN, and F-M2e tandem hPIV2ΔF: an antigen transfer virus for F, from the left to the right.

FIG. 14(A) is a diagram showing that a gene for the fusion of an M2e antigen or an RSV F (including its modified form) extracellular domain and a membrane or intracellular domain of F membrane protein functioning as a viral packaging signal is integrated in the NotI site of an hPIV2/ΔF plasmid. FIG. 14(B) shows results of confirming the expression of M2e in cells infected by a recovered vector.

Figure 1:
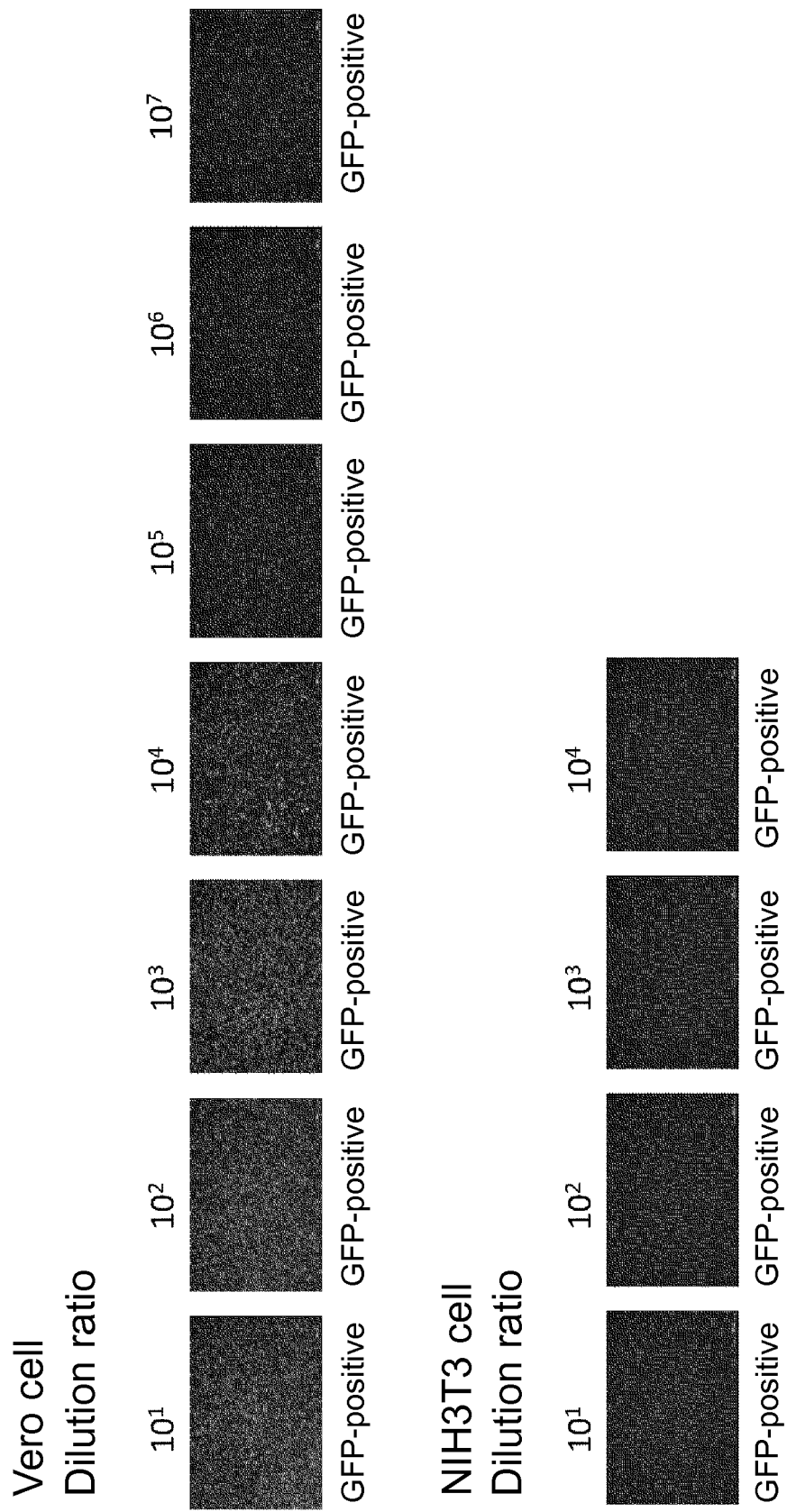
FIG. 1 shows the gene expression efficiency of human parainfluenza virus type 2 in mouse cells (NIH-3T3 cells) and monkey cells (Vero cells). GFP expression was confirmed up to $10^4$ dilutions in the mouse cells and up to 10 dilutions in the monkey cells.

The present specification encompasses the contents described in the specification of Japanese Patent Application No. 2012-283421 on which the priority of the present application is based.

DESCRIPTION OF EMBODIMENTS

In one aspect, the present invention provides a virus vector in which a gene encoding an antigenic polypeptide is integrated in a viral structural gene of the family Paramyxoviridae, wherein the antigenic polypeptide is expressed in the form of a fusion protein with the viral structural protein, and an inactivated vector that is derived from the vector and is capable of inducing immunity similarly to live viruses.

As specifically shown in Examples below, in the present invention, each F gene-defective hPIV2 vector was constructed for expression of a fusion form of universal influenza virus M2e peptide gene, melanoma antigen gp100 peptide gene, or WT-1 cancer antigen gene with F gene-defective hPIV2 vector HN gene and/or F gene. Also, an F gene-defective hPIV2 vector in which an M2e antigen and a packaging signal-containing membrane or intracellular domain of F membrane protein were fused into the foreign gene insertion site of the F gene-defective hPIV2 vector was constructed.

The genomes of these vectors were further inactivated by β-propiolactone treatment in the state where their hemagglutinating activity and ability to mature dendritic cells were maintained. The inactivated or live vectors thus obtained were confirmed to have a very high vaccine effect on influenza viruses and an inhibitory effect on melanoma growth.

The virus of the family Paramyxoviridae used in the present invention is particularly preferably human parainfluenza virus type 2 having monocistronic negative-sense single-stranded RNA of approximately 15,000 bases as the genome. NP protein, P (phospho) protein, M (matrix) protein, F (fusion) protein, HN (hemagglutinin-neuraminidase) protein, and L (large) protein are encoded in this order as viral structural gene products on the genome. In addition, V protein is produced by RNA editing. The nucleocapsid protein (NP) is bound with the RNA genome to form a helically symmetric ribonucleoside-protein complex (nucleocapsid, RNP). Of the proteins encoded on the virus genome, the NP protein, the P (phospho) protein, and the L (large) protein are necessary for the formation of RNP. The F (fusion) protein and the HN (hemagglutinin-neuraminidase) protein reside on the virus envelope and are responsible for adsorption and fusion to a receptor. The M (matrix) protein interacts with the intracytoplasmic domains of the F and HN proteins, the envelope lipid bilayer, and RNP and is important for the budding of virus particles.

Since the human parainfluenza virus type 2 is an RNA virus that multiplies cytoplasmically, its gene is not integrated into the chromosomes of host cells. This virus is known to infect the mucous membrane of the human respiratory tract and induce mucosal immunity consisting of IgA mainly and humoral immunity and cellular immunity mediated by IgG. No serious case of infection of humans (adults) by this virus has previously been reported. The virus is therefore considered to be very useful as a virus vector for treatment.

The "virus vector" means a virus particle by which a gene to be expressed in an infected cell, is packaged together with the virus genome, and a vector of which genome is not capable of producing a virus having infectious ability. In the present specification, the latter is particularly referred to as an "inactivated vector" and can be obtained by inactivating the nucleic acid by treatment with a drug or the like.

The "antigenic polypeptide" refers to a polypeptide that can cause immune response in a subject given the virus vector of the present invention. Examples thereof include cancer antigens or a portion thereof and bacterium- or virus-derived proteins or a portion thereof. For example, the antigenic polypeptide useful for use as a vaccine for influenza is influenza virus HA protein, NA protein, M2 protein, or M2e protein, or a fragment thereof.

Examples of infectious disease-related antigenic polypeptides to be transferred include antigenic peptides of viruses such as influenza viruses (including a highly virulent influenza virus), parainfluenza virus type 3, RS virus, Hendra virus, SARS virus, Nipah virus, Lassa virus, dengue virus, West Nile virus, human metapneumovirus, Ebola virus, hantavirus, AIDS virus, hepatitis C virus, Lassa virus, human papillomavirus, rubella virus, rotavirus, norovirus, Crimean-Congo hemorrhagic fever virus, herpesvirus, cytomegalovirus, and papillomavirus, and antigenic peptides of bacteria such as group A beta-hemolytic *streptococcus, Mycobacterium tuberculosis, Vibrio cholerae,* and *mycoplasma*.

Examples of antigenic polypeptides useful for use as vaccines for cancer treatment include gp100, MUC1, NY-ESO-1, MelanA/MART1, TRP2, MAGE, CEA, CA125, HER2/neu, WT1, and PSA. The fragment refers to a polypeptide that has a partial sequence of the protein to be used as an antigen and can cause immune response when administered to a subject. The immune response includes both humoral immunity and cellular immunity.

In the present invention, the antigenic polypeptide is expressed in the form of a fusion protein with a viral structural protein or a portion of the structural protein. As a result, the antigenic polypeptide expressed in the virus is taken up into the virus particle and delivered to a cell infected by the virus. Specifically, in the present invention, the gene of the antigenic polypeptide integrated on the viral gene is transcribed and translated in the infected cell, and in addition, the virus particle itself has the antigenic polypeptide and can thereby reliably deliver a large amount of the antigenic polypeptide to the recipient cell.

In order to express the antigenic polypeptide expressed in the form of a fusion protein, the gene encoding the antigenic polypeptide is integrated into a viral gene such that the gene encoding the antigenic polypeptide is linked to a gene encoding the viral structural protein or a portion of the structural protein. Examples of the gene encoding the viral structural protein include hPIV2 HN gene, F gene, M gene, NP gene, P gene, and L gene. One type of antigen gene may be used, or two or more types of antigen genes may be linked thereto. This can cause immune response to two or more types of antigens. Alternatively, a plurality of antigens may be transferred simultaneously to a plurality of genes selected from the HN gene, the F gene, the M gene, the NP gene, the P gene, and the L gene. Such a vector can be constructed by a standard method using routine recombinant DNA technique.

Particularly preferably, the antigenic polypeptide is expressed in the form of a fusion protein with one or more selected from HN protein, F protein, and M protein. The integration of the antigen gene such that the antigenic polypeptide is fused on the C-terminal side of the HN protein allows the antigenic polypeptide to be expressed on the virus envelope. The integration of the antigen gene such that the antigenic polypeptide is fused on the N-terminal side of the HN protein, fused on the N- or C-terminal side of the F protein, or fused with the M protein allows the antigenic polypeptide to be expressed inside the virus particle. The F protein fused on its C-terminal side with the antigenic peptide can be constructed and combined with a packaging cell that supplies the protein in trans so that a large amount of the antigen is expressed inside the envelope of F-defective hPIV2. The antigenic peptide can be fused with a membrane or intracellular domain of the HN protein or the F protein of the virus so that the antigen is included on the vector envelope. Since the HN protein or the F protein has antigenicity in itself, high immunogenicity can be imparted to even a low immunogenic antigenic polypeptide by fusion with the HN protein or the F protein.

In a preferred embodiment of the present invention, an F gene-defective (referred to as ΔF) virus is used as the human parainfluenza virus type 2. The F protein of the human parainfluenza virus type 2 is a protein necessary for fusing the virus envelope and a cell membrane and transferring virus nucleocapsid into the host in the virus replication and transcription processes. The F gene-defective human parainfluenza virus type 2 yields infectious hPIV2 carrying the F gene in packaging cells, but does not yield the infectious virus in cells without the expressed F protein. Thus, this virus cannot constitute a virus particle having the ability to multiply autonomously after infection of cells of a subject and does not infect the other cells. The virus is therefore highly safe as a virus for vaccines.

In order to prepare the F gene-defective human parainfluenza virus type 2 vector, an F gene-defective virus is cultured in cells expressing hPIV2 F protein. The F protein can thereby be retained on the virus envelope in the presence of the F protein supplied in trans from the cells to produce virus particles having infectious ability.

In a preferred embodiment of the present invention, Vero cells are used as the packaging cells that can produce virus particles by infection by the F gene-defective virus. The Vero cells are particularly highly permissive with the human parainfluenza virus type 2 F protein. In addition, these cells do not express interferons, and can stably grow and can efficiency produce virus particles, even if the human parainfluenza virus type 2 F gene is constantly expressed.

Instead of the Vero packaging cells expressing the F gene, Vero cells carrying the F gene fused with the antigenic polypeptide can be used as the packaging cells to produce defective virus particles having infectious ability that supplies the F gene in trans.

In another aspect, the present invention provides a method for producing a human parainfluenza virus type 2 vector by which an antigenic polypeptide is expressed in the form of a fusion protein with a viral structural protein. This method comprises the steps of: coculturing, with a Vero cell, human parainfluenza virus type 2 in which a gene encoding the fusion protein is integrated in a viral gene; and isolating a virus particle from the culture supernatant.

In a preferred embodiment, the virus vector of the present invention has undergone nucleic acid inactivation treatment. The nucleic acid inactivation treatment refers to the inactivation of only the virus genome in the state where the three-dimensional structures of envelope proteins such as F protein and HN protein are maintained and these proteins have their functions. The nucleic acid inactivation treatment can be carried out by, for example, nucleic acid-alkylating agent treatment, hydrogen peroxide treatment, UV irradiation, exposure to radiation, or heat treatment. Particularly preferably, the virus vector is treated with a nucleic acid-alkylating agent β-propiolactone. The β-propiolactone can be added to the virus culture solution and incubated therewith at 4° C. for approximately 24 hours. The concentration of the β-propiolactone is preferably 0.004% to 0.05%, more preferably 0.004% to 0.01%, in terms of final concentration.

By use of the F gene-defective virus, the virus lacks the ability to multiply and thus cannot multiply in a recipient even if the live virus remains after the drug treatment; thus, the high safety of the inactivated vaccine can be kept.

The treatment of the virus vector of the present invention with β-propiolactone can inactivate the genome while the virus vector maintains its hemagglutinating activity and ability to maturate dendritic cells. This method has the advantage that: the virus particle itself has adjuvant activity and therefore eliminates the need of combined use with an adjuvant that causes immunity against the antigen or can reduce adjuvant concentration.

The virus vector of the present invention infects a cell via a sialic acid receptor. Since sialic acid resides on the surface of many cells or tissues, the possible administration route of the vector is nasal spray, transpulmonary, oral, sublingual, intradermal, or subcutaneous administration, or direct administration to the vein as well as ex vivo administration to immunity-causing cells such as dendritic cells.

Typically, the virus vector of the present invention can be administered as an aerosol to cells of a mammal including a human. The aerosol can be prepared by a standard method. For example, a culture supernatant containing the virus vector is concentrated, if necessary, and suspended together with an appropriate carrier or excipient in a buffer solution such as PBS, a virus vector-stabilizing solution, or saline. Then, the suspension can be sterilized by filtration through a filter or the like according to the need and subsequently charged into an aseptic container to prepare the aerosol. The aerosol may be supplemented with a stabilizer, a preservative, and the like, according to the need. The expression vector thus obtained can be administered by inhalation to a subject.

Typically, the virus vector of the present invention can also be administered as an injection (subcutaneous, intradermal, or intramuscular injection) to cells of a mammal including a human. The injection can be prepared by a standard method. For example, a culture supernatant containing the virus vector is concentrated, if necessary, and suspended together with an appropriate carrier or excipient in a buffer solution such as PBS or saline. Then, the suspension can be sterilized by filtration through a filter or the like according to the need and subsequently charged into an aseptic container to prepare the injection. The injection may be supplemented with a stabilizer, a preservative, and the like, according to the need. The expression vector thus obtained can be administered as the injection to a subject.

Hereinafter, the present invention will be described in more detail with reference to Examples. However, the present invention is not intended to be limited by these Examples.

EXAMPLES

Example 1 Confirmation of Transgene Expression in African Green Monkey Cell (Vero Cell) and Mouse Cell (NIH3T3 Cell) Using hPIV2/ΔF Vero cells or NIH3T3 cells were cultured in a 96-well plate such that the cells became a monolayer at the time of vector infection. hPIV2/ΔF harboring GFP gene was diluted up to $10^8$ from the undiluted solution. This vector does not yield an infectious vector and therefore exhibits GFP fluorescence only in primarily infected cells. The virus dilutions were each added at 1/10 of the amount of each cell culture solution, followed by culture for 3 days.

As a result, the GFP fluorescence was confirmed in the Vero cells and the NIH3T3 cells when $10^1$ to $10^7$ vector dilutions and $10^1$ to $10^4$ vector dilutions, respectively, were added thereto (FIG. 1).

Example 2 Confirmation of the Number of Multiplied Vector Copy in Human and Mouse Dendritic Cell Using hPIV2/ΔF (Preparation of Human Dendritic Cells)
Under the code of ethical conduct, CD14-positive cells were recovered from the peripheral blood of a healthy person. At cell culture days 1, 4, and 7, 50 ng/mL GM-CSF and 25 ng/mL IL-4 were added to the culture solution to culture the cells. The cells cultured for 8 days were infected at a multiplicity of infection (MOI) of 25, 50, or 100 by hPIV2/ΔF harboring GFP gene. The N gene domain portion of hPIV2 in the cells thus infected for 3 days was subjected to quantitative PCR to measure the number of genome copies.

Figure 2:
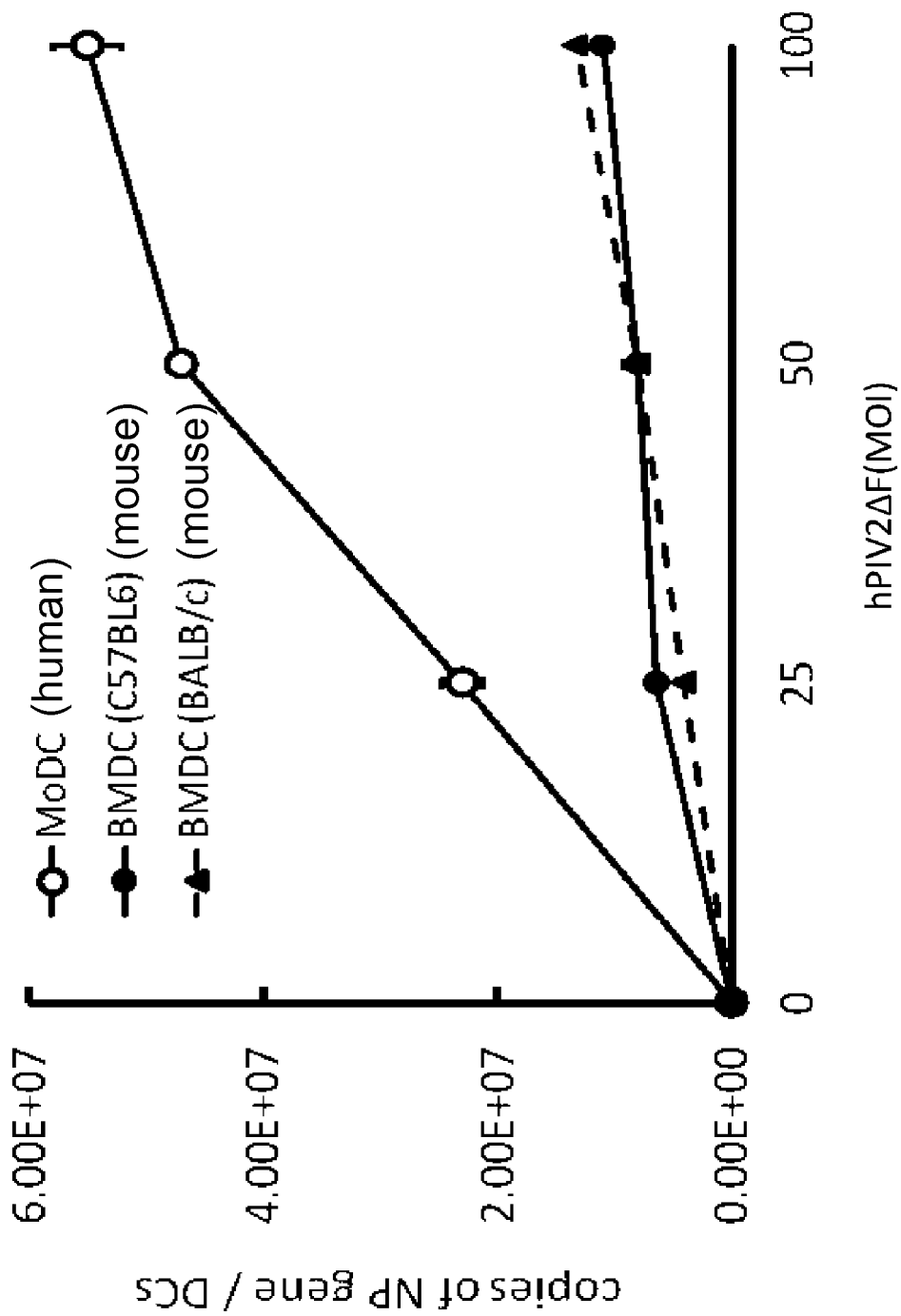
FIG. 2 shows the number of hPIV2/ΔF copies in human and mouse dendritic cells.

(Preparation of Mouse Dendritic Cells)
Under the code of ethical conduct, the bone marrow was recovered from each of the femurs of B57BL/6 and BALB/c mice and cultured (RPM-1640 medium, 10% FBS) after removal of debris. Every two culture days, the culture solution was replaced with a fresh medium, and GM-CSF (20 ng/mL) and IL-4 (20 ng/mL) were added thereto. The cells cultured for 8 days were infected at a multiplicity of infection (MOI) of 25, 50, or 100 by hPIV2/ΔF harboring GFP gene. The N gene domain portion of hPIV2 in the cells thus infected for 3 days was subjected to quantitative PCR to measure the number of genome copies. The results of the quantitative PCR using the N domain portion revealed that the number of copies of the N domain portion per cell was approximately 5 times larger at the maximum in the human dendritic cells compared with the mouse dendritic cells (FIG. 2).

From Examples 1 and 2, hPIV2 was confirmed to be capable of infecting the mouse cells and multiplying the transgene. However, the transgene expression level and the number of multiplied viruses were both low in the mouse cells compared with the human or monkey cells (FIGS. 1 and 2).

Example 3 Confirmation of Infection Efficiency in Dendritic Cells Using hPIV2/ΔF Under the code of ethical conduct, CD14-positive cells were recovered from the peripheral blood of a healthy person. At cell culture days 1, 4, and 7, 50 ng/mL (in terms of final concentration) GM-CSF and 25 ng/mL (in terms of final concentration) IL-4 were added to the culture solution to culture the cells. The cells cultured for 8 days were infected at a multiplicity of infection (MOI) of 25, 50, or 100 by hPIV2/ΔF harboring GFP gene.

Under the code of ethical conduct, the bone marrow was recovered from the femur of B57BL/6 and cultured (RPM-1640 medium, 10% FBS) after removal of debris. Every two culture days, the culture solution was replaced with a fresh medium, and 20 ng/mL (in terms of final concentration) GM-CSF and 20 ng/mL (in terms of final concentration) IL-4 were added thereto. The cells cultured for 8 days were infected at a multiplicity of infection (MOI) of 25, 50, or 100 by hPIV2/ΔF harboring GFP gene.

The infection efficiency in the dendritic cells thus infected for 2 days was examined by flow cytometry with GFP fluorescence as an index. CD11c-positive cells were used as the dendritic cells.

Figure 3:
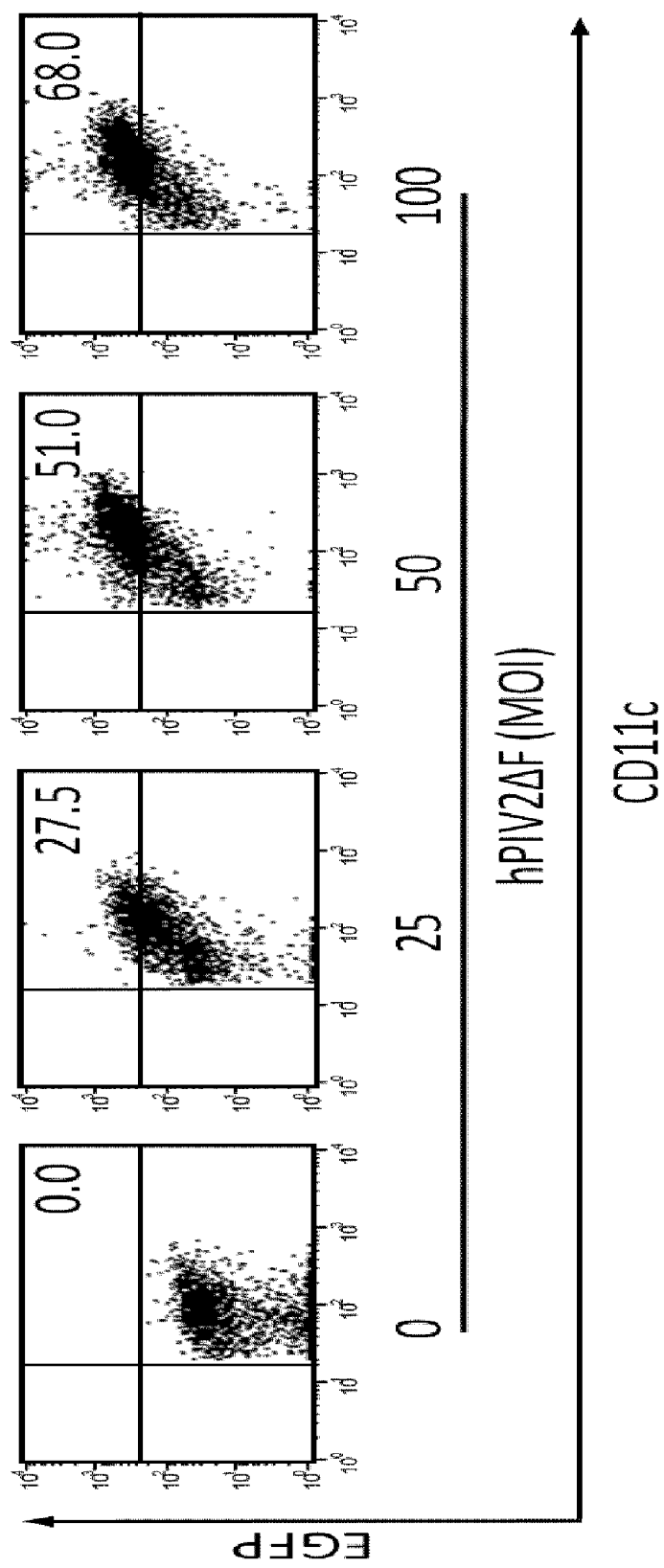
FIG. 3 shows the infection efficiency of hPIV2/ΔF in mouse dendritic cells.

The results about the mouse are shown in FIG. 3. 27.5%, 51.0%, and 68.0% mouse dendritic cells were GFP fluorescence-positive at MOI=25, MOI=50, and MOI=100, respectively (FIG. 3). 59.9%, 73.1%, and 77.8% human dendritic cells were GFP fluorescence-positive at MOI=25, MOI=50, and MOI=100, respectively.

These results demonstrated that: hPIV2/ΔF can infect the human dendritic cells and the mouse dendritic cells and express the gene; and its infection efficiency is higher in the human dendritic cells than in the mouse dendritic cells.

Example 4 Maturation of Human Dendritic Cells by hPIV2/ΔF

In Example 3, hPIV2/ΔF was confirmed to be able to efficiently express the gene in the human dendritic cells. For the effective functions of dendritic cells as immune-presenting cells and the efficient induction of immunity, it is very important that the cells are maturated and homed to lymphoid organs. Thus, human dendritic cells were infected for 2 days by hPIV2/ΔF at MOI=25. The ability to maturate the dendritic cells was evaluated on the basis of the expression of costimulatory factors CD40, CD80, and CD86 for antigen-presenting cells. The ability to home the cells to secondary lymphoid organs was evaluated with a rise in CCR7 expression as an index. As a positive control, LPS (lipopolysaccharide) known to activate TRL4 and very efficiently cause maturation and homing to lymphoid organs was added at 1 μg/mL into the medium. The evaluation was conducted by flow cytometry using an index antibody.

Figure 4:
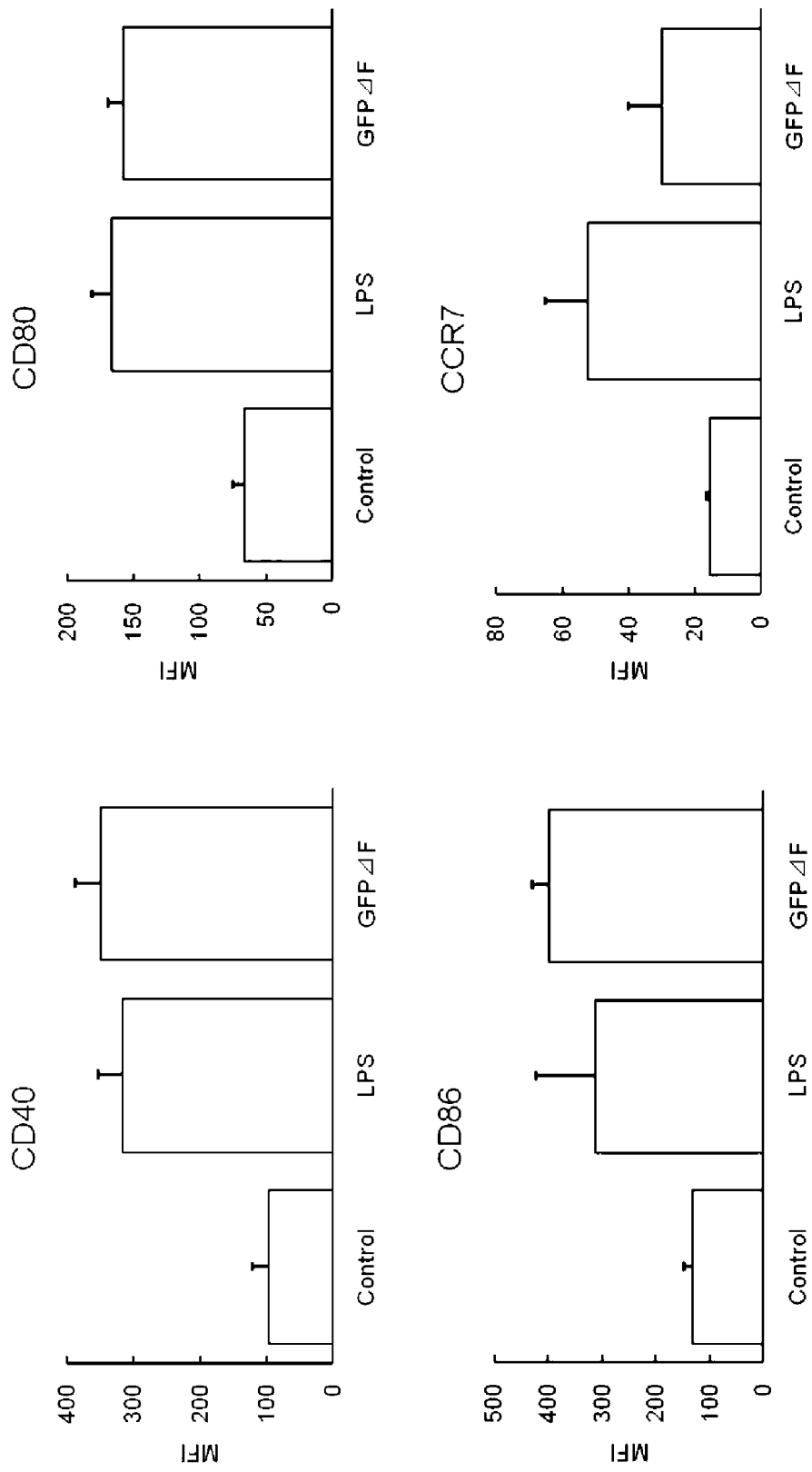
FIG. 4 shows the maturation marker expression of human dendritic cells after live hPIV2/ΔF/GFP infection.

As a result, the dendritic cells infected by hPIV2/ΔF were able to induce the expression of the costimulatory factors at a degree comparable to LPS and exhibited a rise in CCR7 expression (FIG. 4).

Example 5 Major Histocompatibility Complex (MHC, or HLA for Humans) Expression in Human Dendritic Cell and Induction of Cytokine Using hPIV2/ΔF Antigen presentation on MHC is important for the induction of antigen-specific immunity. In this respect, antigen presentation on MHC class I or II molecules is necessary. CD8-positive T cells recognize an antigen on the MHC class I molecule and induce cytotoxic T cells or the like. CD4-positive T cells recognize an antigen on the MHC class II molecule and are activated.

The dendritic cells are capable of presenting an antigen on the MHC class I molecule and the MHC class II molecule. hPIV2/ΔF was examined for a rise in the expression of the MHC class I molecule (or HLA-A molecule for humans) and the MHC class II molecule (or HLA-DR molecule for humans) in human dendritic cells under the same conditions as in Examples 3 and 4 with the human HLA-A molecule as the MHC class I molecule and the human HLA-DR molecule as the MHC class II molecule as indexes. As a result, hPIV2/ΔF also elevated the expression of the HLA-A molecule and the HLA-DR molecule at the same degree as in the positive control LPS (FIG. 5).

Figure 5:
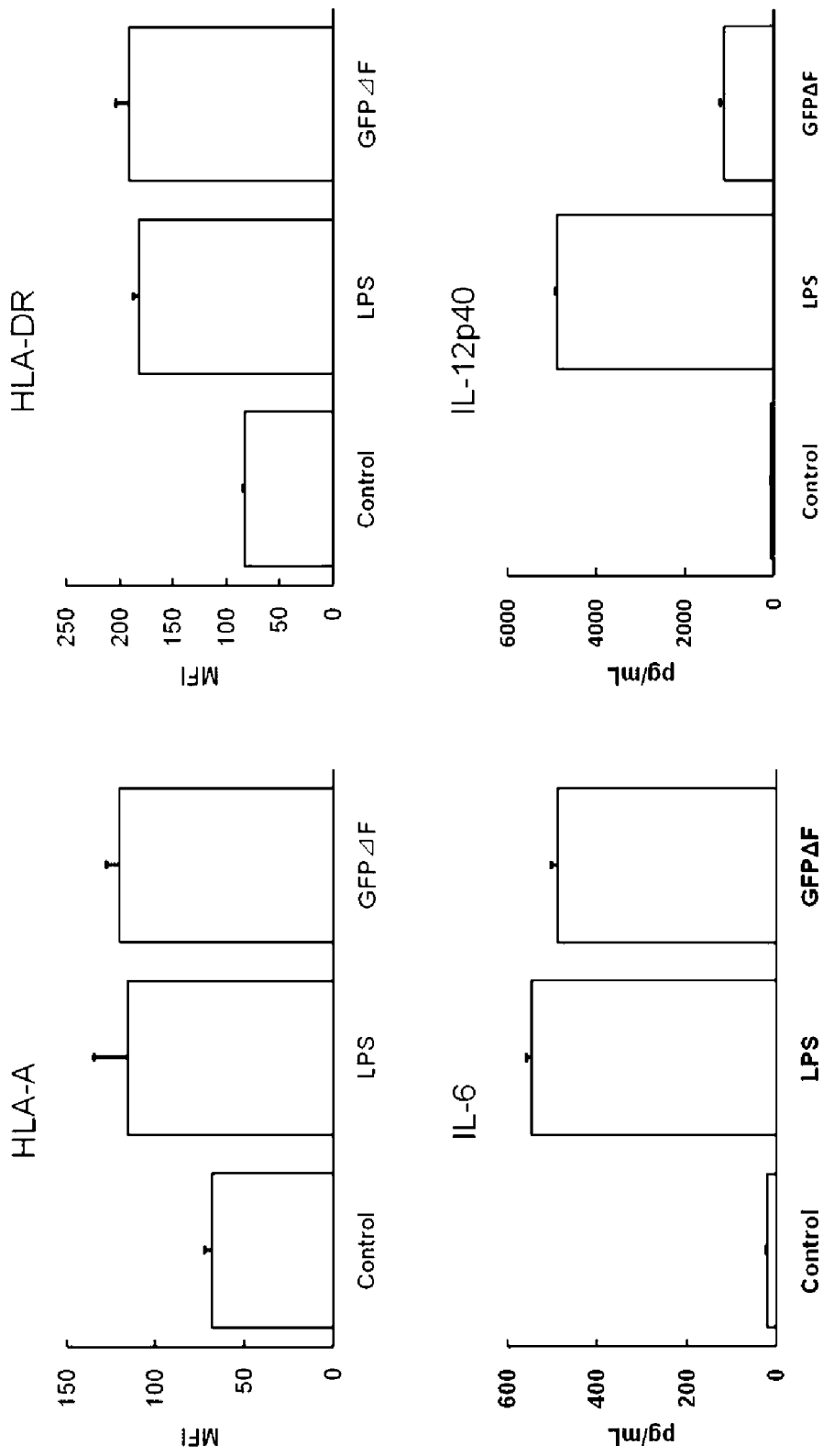
FIG. 5 shows the MHC and cytokine expression of human dendritic cells after live hPIV2/ΔF/GFP infection.

The induction of IL-6 and IL-12 cytokines in a culture supernatant was further examined. hPIV2/ΔF was confirmed to elevate the expression of IL-6 at the same degree as in LPS and the expression of IL-12, albeit at a degree lower than that of LPS, in the human dendritic cells (FIG. 5).

Example 6 Inactivation and Hemagglutinating Activity of hPIV2/ΔF and Induction of Immunity by Inactivated hPIV2/ΔF In order to inactivate only the genome of hPIV2/ΔF with the structures and functions of its proteins maintained, inactivation using an alkylating agent β-propiolactone (BPL) was studied. BPL was added at 0.004%, 0.005%, 0.0075%, 0.009%, 0.01%, 0.012%, 0.025%, or 0.05% to the culture solution of GFP gene-containing hPIV2/ΔF cultured in a serum-free medium, followed by treatment at 4° C. for 24 hours. Then, BPL was inactivated by treatment at 37° C. for 30 minutes. hPIV2/ΔF was recovered by ultracentrifugation. As a control, the same volume of hPIV2/ΔF was also concentrated by ultracentrifugation, and the final volume was suspended in the same volume of a PBS solution. Cells expressing hPIV2 F were infected by the inactivated vector or the control vector and cultured for 10 days. Fresh cells expressing hPIV2 F were further infected by each supernatant and cultured for 10 days. This operation was further carried out. The culture of the F-expressing cells infected by the vector was performed a total of three times. Virus assay by TCID50 also produced similar results.

As a result, the control vector exhibited strong fluorescence and cytopathicity, whereas none of the vectors inactivated by 0.004%, 0.005%, 0.0075%, 0.009%, 0.01%, 0.01%, 0.012%, 0.025%, or 0.05% BPL exhibited GFP fluorescence or cytopathicity. These results demonstrated that the genome is completely inactivated by the BPL treatment (FIG. 6A).

Next, the inactivated vector and the control vector were examined for their hemagglutination reaction. To a 1% guinea pig erythrocyte solution, the same amount of each vector dilution was added to examine the hemagglutination reaction.

Figure 6:
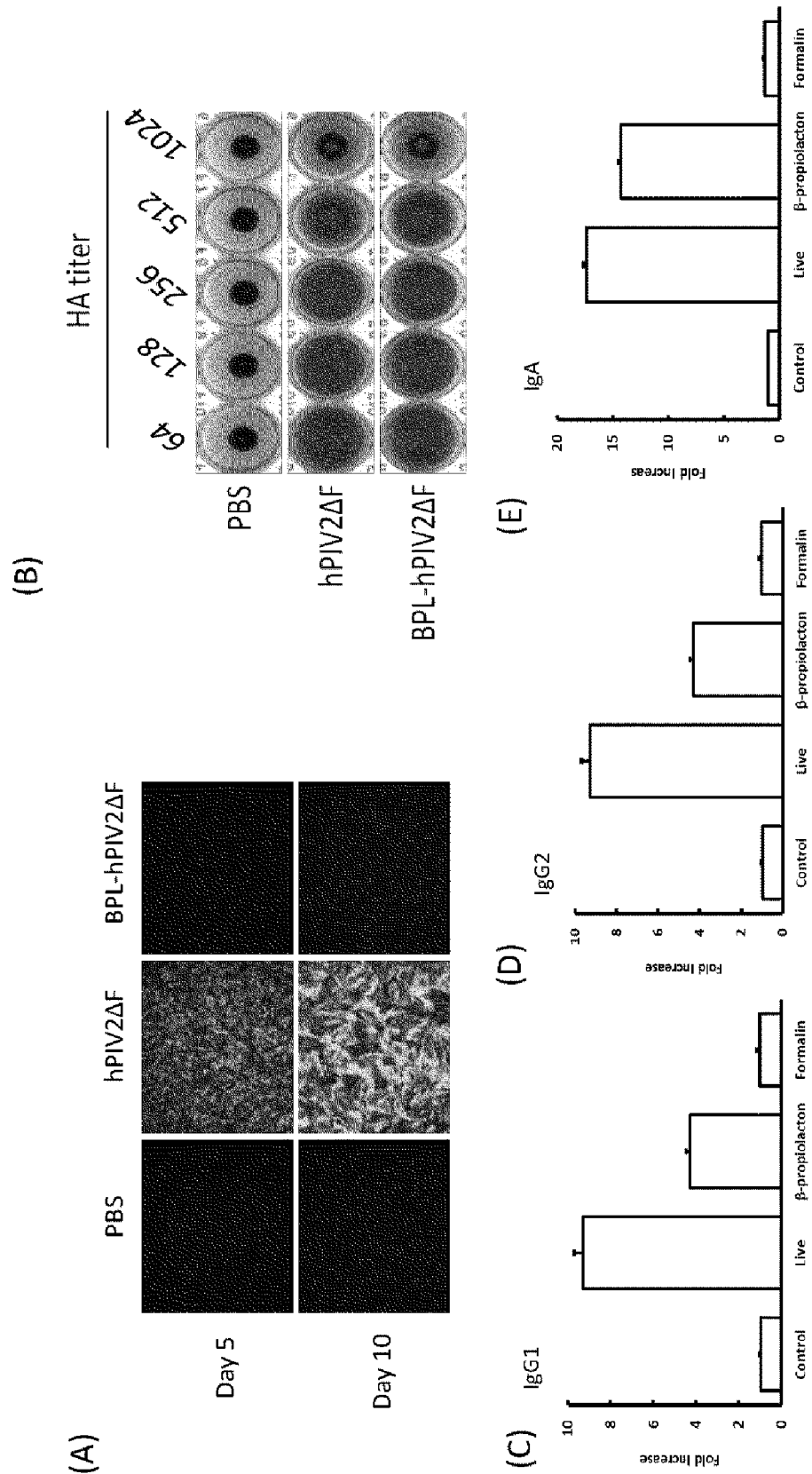
FIG. 6 shows results of virus inactivation treatment with β-propiolactone.

As a result, the inactivated vector exhibited the same 512 HA titer as that of the live hPIV2/ΔF control vector without the inactivation treatment (FIG. 6B). This indicates that the HN protein of the inactivated vector does not lose its hemagglutinating capacity at all, i.e., maintains its three-dimensional structure and does not lose its functions. Thus, only the genome of the vector was presumably inactivated by the inactivation treatment.

In order to examine the effect of inactivation, the vector was inactivated using 0.012% BPL or formalin treatment according to the conventional method. $2 \times 10^7$ vector particles each of live hPIV2/ΔF/GFP, BPL-inactivated hPIV2/ΔF/GFP, and formalin-treated hPIV2/ΔF/GFP were transnasally administered twice (every other week) to a B6 mouse. One week after the administration, alveolar lavages were recovered and examined for antibody titers (IgG1, IgG2, and IgA) against the vectors. A 96-well plate was coated with 4 μg/mL inactivated hPIV2, and the antibody titers were measured. As a result, BPL-inactivated hPIV2/ΔF/GFP in the alveolar lavage induced IgG1, IgG2, and IgA antibodies, albeit at a degree lower than that of live hPIV2/ΔF/GFP. A rise in antibody against formalin-treated hPIV2/ΔF/GFP was hardly seen in the alveolar lavage (FIGS. 6C, 6D, and 6E). This indicates that the induction of antibodies against the hPIV2 proteins having a normal three-dimensional structure was low in the alveolar lavage by the formalin treatment. On the other hand, a rise in antibody was observed even for formalin-treated hPIV2/ΔF as a result of stimulation with an antigen for a long period using spleen cells. From these results, the vector treated with a low concentration of BPL was confirmed to induce antibodies similarly to live viruses, as compared with the formalin treatment. From these results, it was presumed that the membrane protein structures similar to those of live viruses can be maintained after the inactivation treatment with a low concentration of BPL compared with the formalin treatment.

Example 7 Maturation of Mouse Dendritic Cell, Major Histocompatibility Complex (MHC or HLA for Humans) Expression, and Induction of Cytokine Using hPIV2/ΔF The bone marrow was recovered from the femurs of B57BL/6 mice. At cell culture days 1, 4, and 7, 25 ng/mL GM-CSF was added to the culture solution to culture the cells. The cells cultured for 8 days were infected at a multiplicity of infection (MOI) of 25 by the GFP gene-containing vector hPIV2/ΔF inactivated by treatment with 0.05% BPL. The maturation of dendritic cells based on the elevated expression of CD40 and CD80, a rise in MHC class I or II based on H-2K$^b$ and I-A/I-E, and the expression of IL-6 and IL-12 in the culture solution were examined in the cells thus infected for 2 days. (Live) hPIV2/ΔF without inactivation was used as a control.

Figure 7:
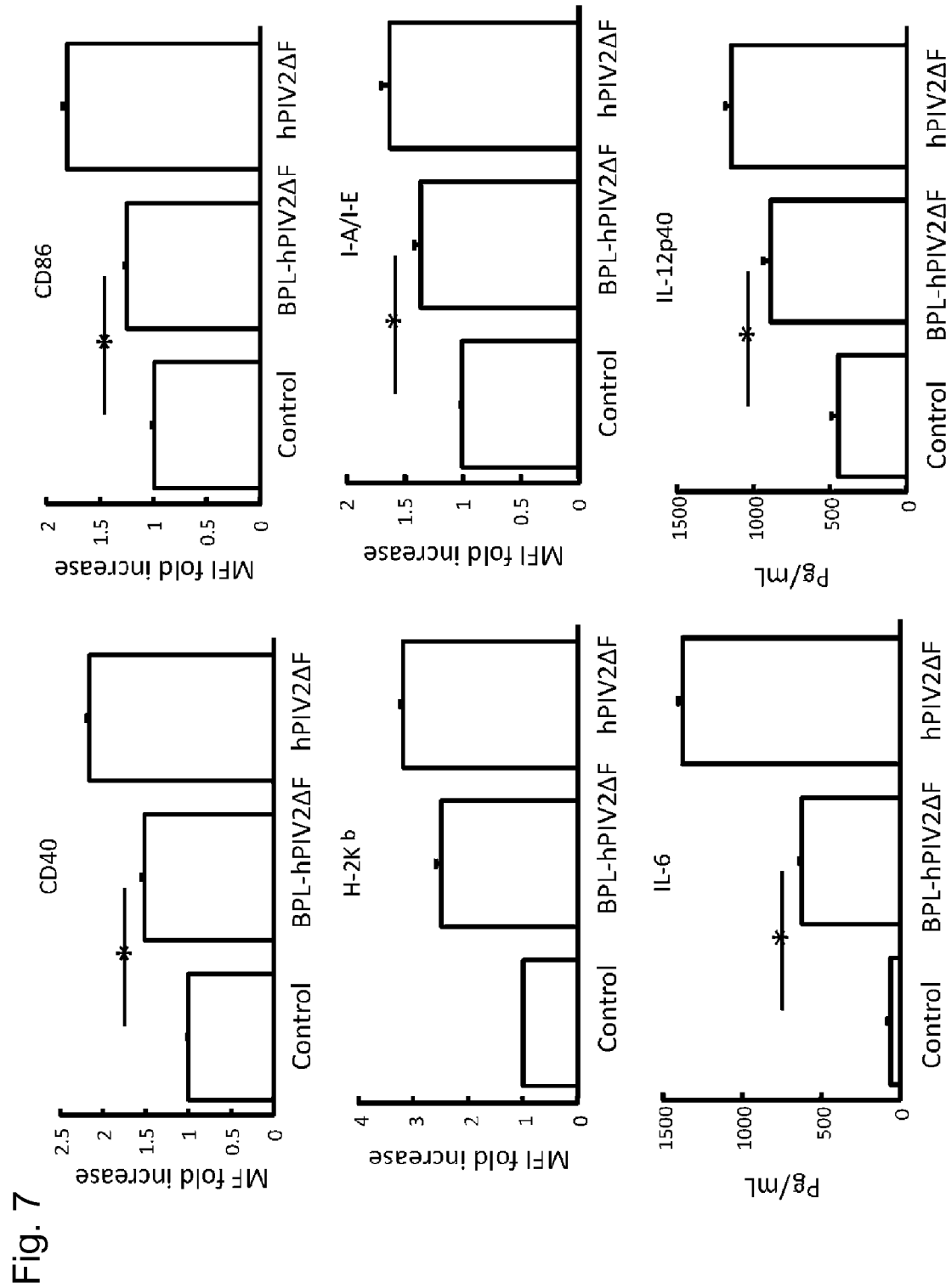
FIG. 7 shows the maturation and MHC expression of mouse dendritic cells and the induction of cytokines by live and β-propiolactone (BPL)-inactivated hPIV2/ΔF.

As a result, the infection of the mouse dendritic cells by hPIV2/ΔF was confirmed to elevate the expression of the CD40 and CD86 maturation markers, though their expression levels were low as compared with live hPIV2/ΔF (FIG. 7). The infection by the vector hPIV2/ΔF inactivated by treatment with 0.012% BPL at a multiplicity of infection (MOI) of 25 produced an effect equivalent to that of (live) hPIV2/ΔF.

The expression of the mouse H-2K$^b$ molecule corresponding to the MHC class I molecule and the I-A/I-E molecule corresponding to the MHC class II molecule was also elevated. The secretion of each cytokine was also elevated, albeit at a degree lower than that of live hPIV2/ΔF (FIG. 7). The infection by the vector hPIV2/ΔF inactivated by treatment with 0.012% BPL at a multiplicity of infection (MOI) of 25 produced an effect equivalent to that of (live) hPIV2/ΔF.

From these results, bot live and inactivated vectors of hPIV2/ΔF were confirmed to be usable in vector evaluation and therefore subjected to the following tests.

Example 8 Construction of hPIV2/ΔF in which Antigen Gene was Fused with hPIV2 HN Gene A plasmid construct of a vector was constructed such that universal influenza virus M2e antigenic peptide (N terminus-SLLTEVETPIRNEWGCRCNDSSDD-C terminus (SEQ ID NO: 1)) or skin cancer malignant tumor gp-100 antigenic peptide (N terminus-KVPRNQDWL-C terminus (SEQ ID NO: 2)) was inserted to the C-terminal tail portion of hPIV2 HN protein. This construct was constructed on the basis of the rule of 6 reportedly important for the construct such that the total number of hPIV2 genomes was a multiple of 6. The virus was recovered by the reverse genetics method.

Figure 8:
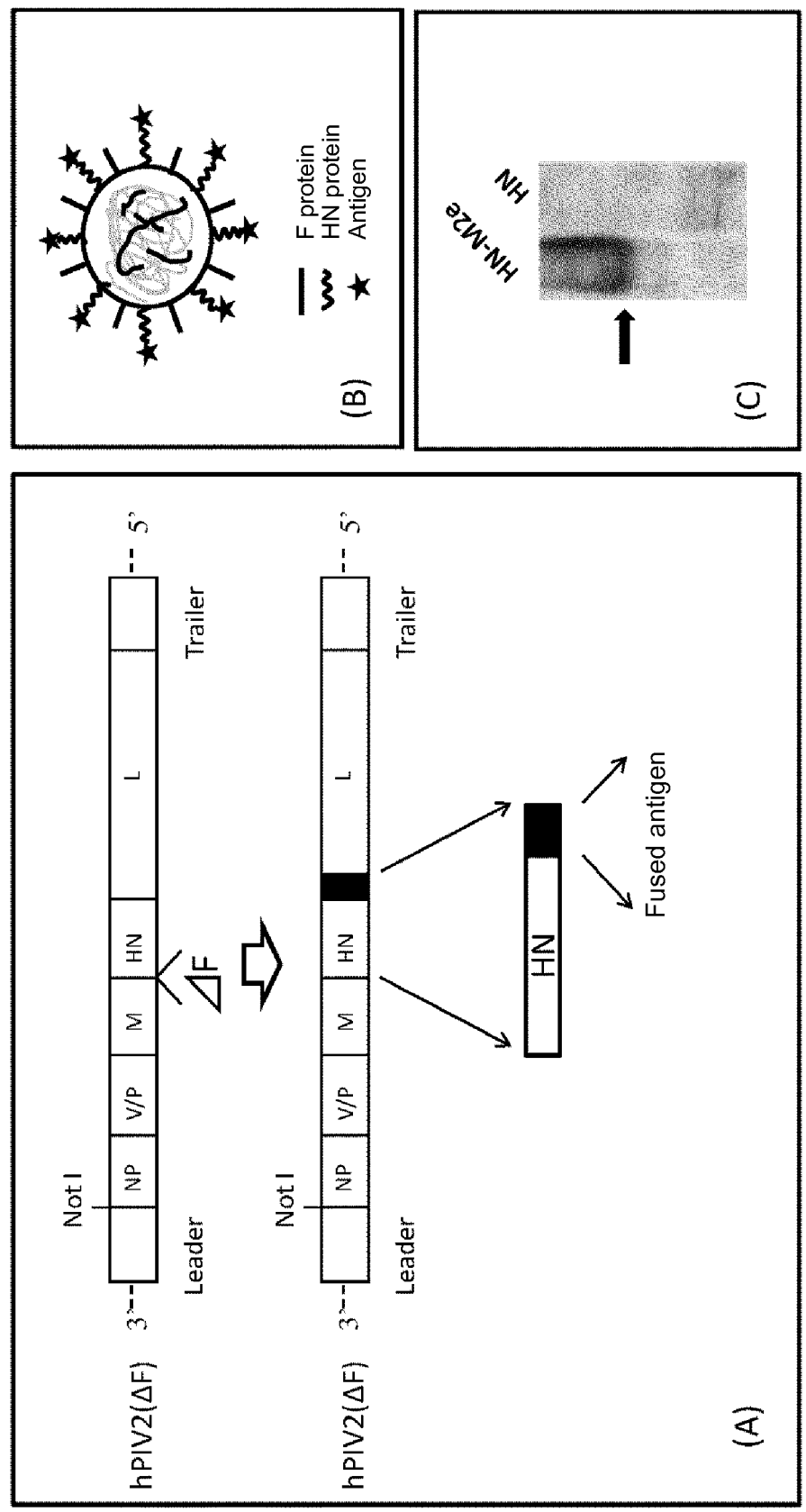
FIG. 8 shows the construction of a vector for producing a fusion protein between an antigen and hPIV2 HN.

As a result, hPIV2/ΔF/HN-M2e and hPIV2/ΔF/HN-gp-100 in which the universal influenza virus M2e antigenic peptide or the skin cancer malignant tumor gp-100 antigenic peptide was fused with the HN gene were successfully recovered (FIG. 8). The transfer of a gene encoding M2e antigenic peptide [N terminus-SLLTEVETPTRNEWECRC-SDSSDD-C terminus (SEQ ID NO: 7) or N terminus-SLLTEVETLTRNGWGCRCSDSSDD-C terminus (SEQ ID NO: 8)] or WT-1 [N terminus-ALLPAVPSL-C terminus (SEQ ID NO: 3), N terminus-CYTWNQMNL-C terminus (SEQ ID NO: 4), N terminus-CMTWNQMNL-C terminus (SEQ ID NO: 5), or N terminus-RMPNAPYL-C terminus (SEQ ID NO: 6)] was also carried out. However, the recovery of the vector harboring the highly hydrophobic peptide (e.g., N terminus-CYTWNQMNL-C terminus (SEQ ID NO: 4)) was also found to be difficult, as compared with the recovery of common hPIV2/ΔF. There is no report on the expression of an antigen in a fusion form from a defective virus vector of the family Paramyxoviridae.

Example 9 Construction of Packaging Cell Expressing Fusion Product of Antigen Gene with F Gene and Construction of hPIV2/ΔF A gene encoding universal influenza virus M2e antigenic peptide (N terminus-SLLTEVET-PIRNEWGCRCNDSSDD-C terminus: SEQ ID NO: 1), WT-1 antigenic peptide (N terminus-ALLPAVPSL-C terminus (SEQ ID NO: 3)), WT-1 antigenic peptide (N terminus-CYTWNQMNL-C terminus (SEQ ID NO: 4)), or WT-1 antigenic peptide (N terminus-RMPNAPYL-C terminus (SEQ ID NO: 6)) was integrated on the 3'-terminal side of hPIV2 F gene on a plasmid for F expression constructed in order to prepare packaging cells. In this way, the packaging cells were constructed. One or more antigens were transferred thereto. The cells were used to recover F-defective hPIV2 by the conventional reverse genetics method.

Figure 9:
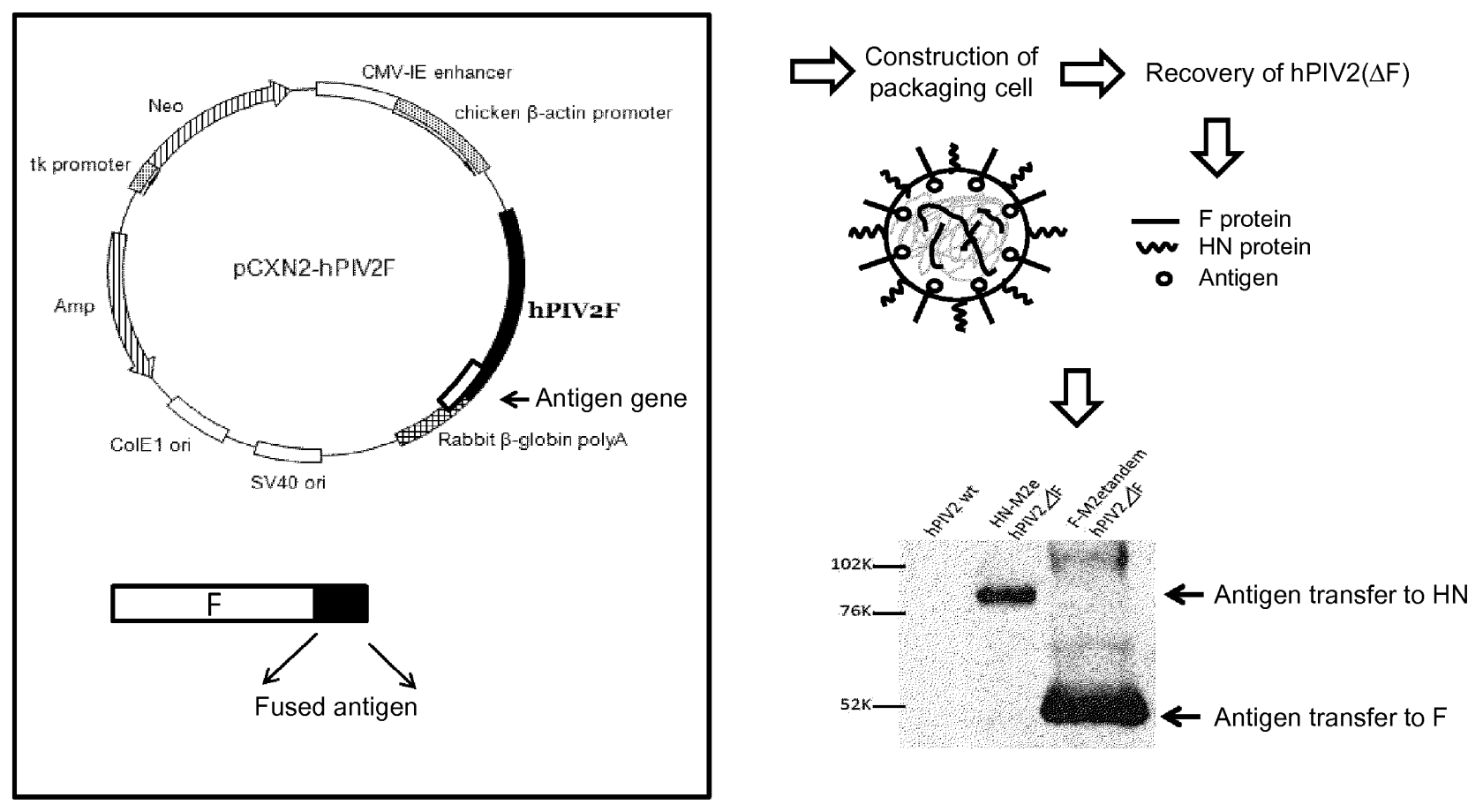

As a result, as shown in FIG. 9, a vector carrying the antigen inside the vector was successfully recovered. Also, an expression vector for a plurality of antigens was successfully recovered. The recovery of a vector for antigen expression inside the vector envelope was also found to be easier than the recovery of a vector for antigen expression outside the vector envelope. The transfer of a gene encoding M2e antigenic peptide [N terminus-SLLTEVETPTRNEWECRC-SDSSDD-C terminus (SEQ ID NO: 7) or N terminus-SLLTEVETLTRNGWGCRCSDSSDD-C terminus (SEQ ID NO: 8)] or WT-1 peptide (N terminus-CMTWNQMNL-C terminus (SEQ ID NO: 5)) was also carried out.

Example 10 Construction of Vector Capable of Antigen Expression Both Inside and Outside F-Defective hPIV2 Envelope Examples 8 and 9 showed the recovery of the vector capable of antigen expression inside or outside the vector envelope. In this Example, the recovery of F-defective hPIV2 carrying antigens both inside and outside the vector was studied. The F packaging cells in which two M2e genes were fused with F gene as shown in Example 9 were infected by the M2e antigen (SEQ ID NO: 1)-carrying vector recovered in Example 8. Whether the vector could be recovered was examined.

Figure 10:
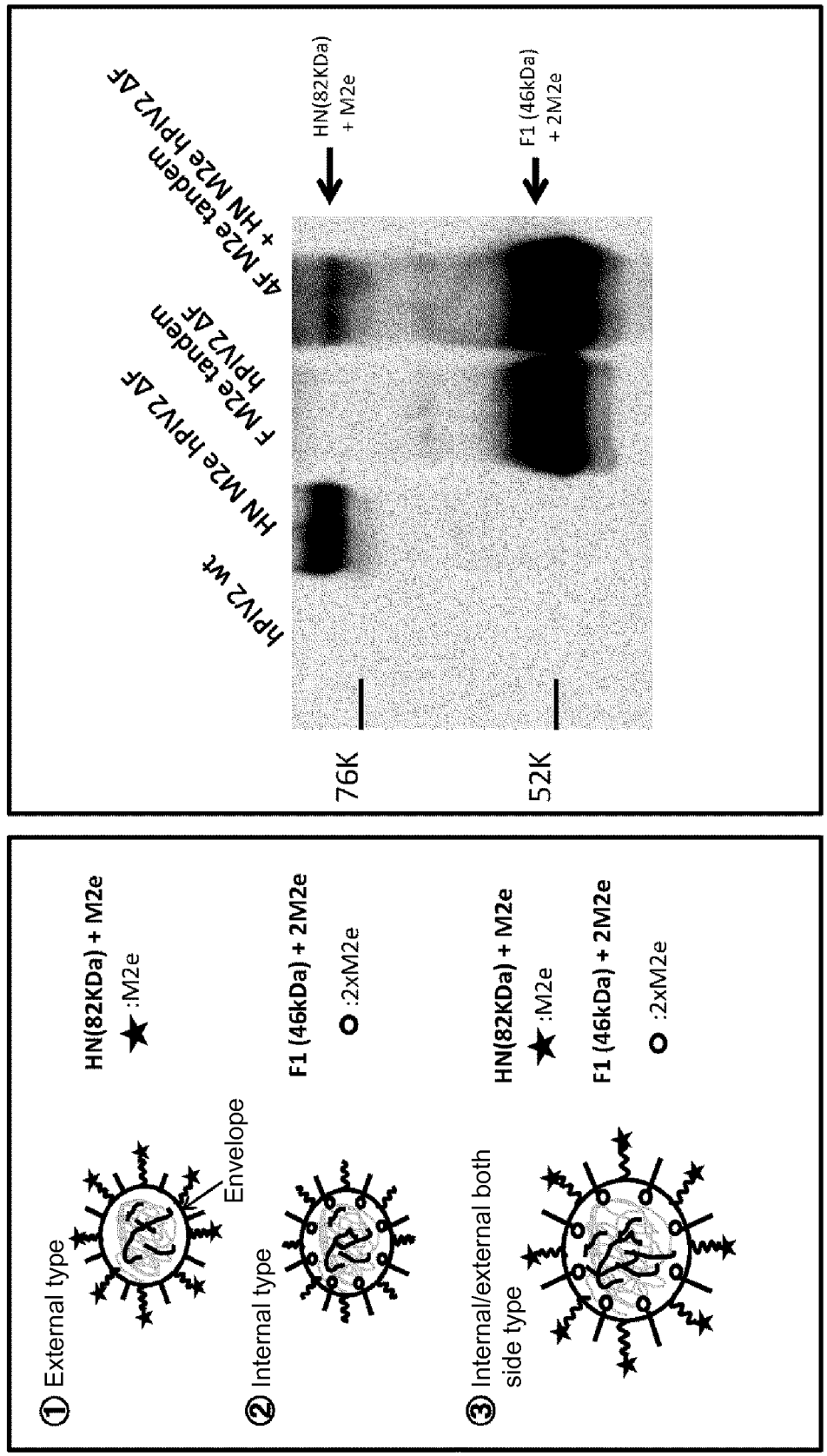
FIG. 10(A) shows the mode of antigen transfer to hPIV2 (diagram showing the arrangement of a vector and an antigen).
FIG. 10(B) shows results of antigen transfer by a vector that simultaneously transferred the antigen to HN and F (Western blot). The Western blot images depict hPIV2 wt: an antigen transfer-free virus, HN-M2e hPIV2ΔF: an antigen transfer virus for HN, F M2e tandem hPIV2ΔF: an antigen transfer virus for F, 4F M2e tandem+HN M2e hPIV2ΔF: and an antigen transfer virus for both F and HN, from the left to the right.

As a result, as shown in FIG. 10, two types of proteins reacting with anti-M2 antibodies were detected by the Western blot of the vector recovered from 3 mL of a viral infection culture supernatant. Their molecular weights corresponded to the total molecular weights of the F protein (cleaved F protein) and the HN protein with the M2e antigen, demonstrating that the vector carrying antigens outside and inside the envelope was successfully recovered. From FIG. 10, the band of F protein-fused M2e was thicker than that of HN protein-fused M2e, demonstrating that the F protein supplied in trans from the packaging cells and the antigen are present in larger amounts on the vector.

Example 11 Vaccine Effect of hPIV2/ΔF/HN-M2e on Influenza Virus hPIV2/ΔF/HN-M2e for expression of a fusion form of an influenza M2e antigen (SEQ ID NO: 1) with HN protein was examined for its preventive effect on an influenza RP8 strain. Each of live hPIV2/ΔF/HN-M2e and hPIV2/ΔF/HN-M2e inactivated by treatment with 0.05% BPL was used as the hPIV2/ΔF/HN-M2e. In addition, live hPIV2/ΔF/M2 for expressing the whole of M2 by itself was used for comparison. In HN-fused M2e, the N-terminal region of HN resides inside the membrane of the virus envelope, while the C-terminal region resides outside the membrane.

In this experiment, whether M2e constructed in a fusion form with HN in hPIV2/ΔF/HN-M2e was recognized as an antigen and whether inactivated hPIV2/ΔF/HN-M2e was effective as a vaccine were examined.

Under the code of ethical conduct, the test was conducted using 5-week-old female BALB/c. $2\times10^8$ vector particles each of live hPIV2/ΔF/HN-M2e, inactivated hPIV2/ΔF/HN-M2e, live hPIV2/ΔF/M2, and inactivated hPIV2/ΔF/GFP were transnasally administered at a dose of 20 μl (in terms of TCID50) to the mouse under anesthesia. This administration was carried out again after 2 weeks. Two weeks after the administration, 16,000 influenza viruses of the PR8 strain (LD50: 1,000 viruses or less) were transnasally administered at a dose of 20 μl to each mouse of the vector administration group and the control group under anesthesia. Body weight measurement and external observation were carried out every day from the administration date. Dead mice or mice whose body weight was decreased by 30% compared with that at the time of influenza virus inoculation were regarded as being dead.

Figure 11:
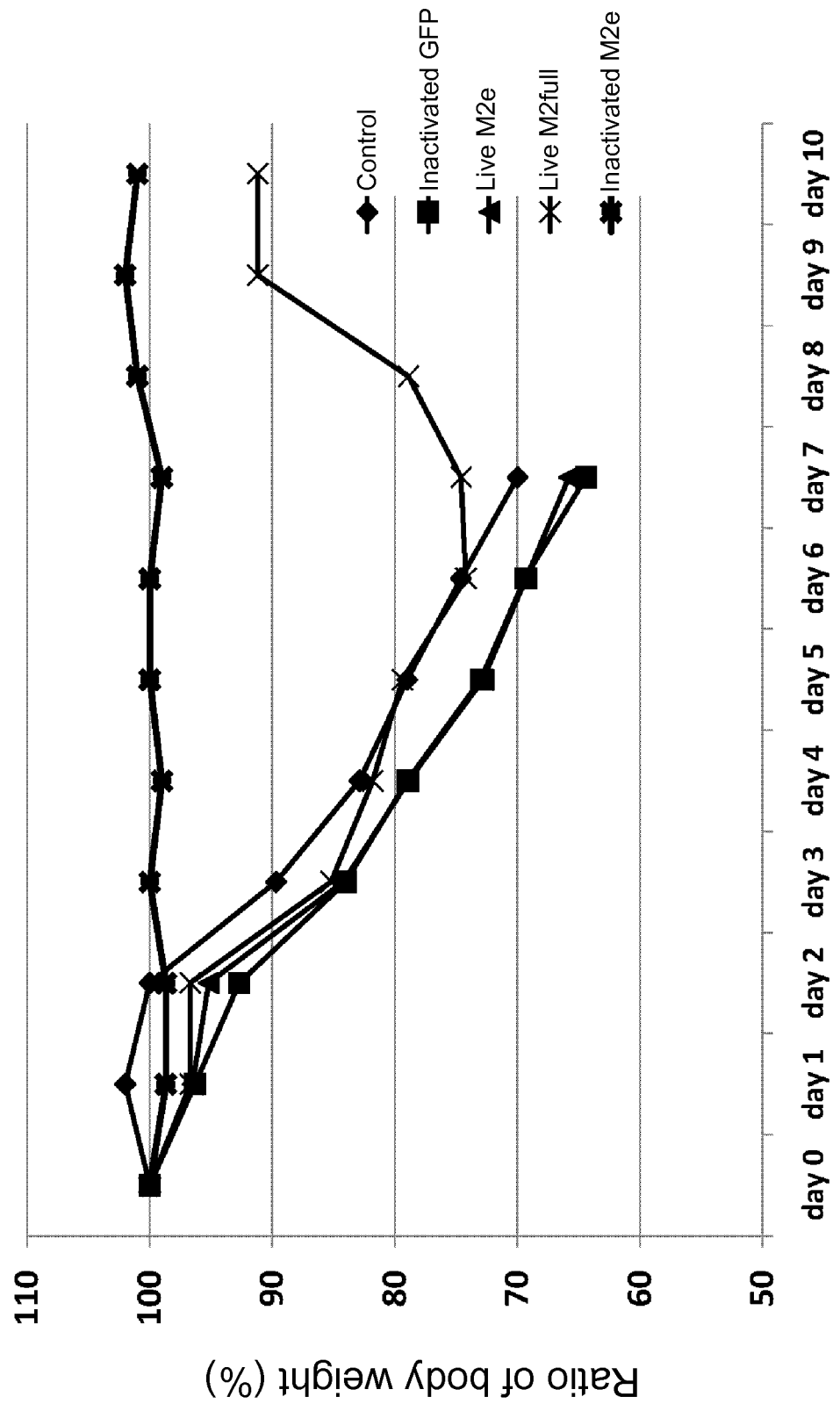
FIG. 11 shows the vaccine effect of hPIV2/ΔF/HN-M2e against an influenza virus infection.

FIG. 11 shows the results about body weight change (in percentage) and deaths for 10 days after the influenza virus inoculation. Very surprisingly, all of the mice in the inactivated hPIV2/ΔF/HN-M2e group (n=4) exhibited neither reduction in body weight nor piloerection even after the influenza virus administration, and their movement and feeding did not vary from those before the virus administration.

On the other hand, one of the 3 mice given live hPIV2/ΔF/M2 made a recovery, whereas the other mice died. Particularly, live hPIV2/ΔF/M2 decreased the average body weight by nearly 2 g at the maximum at the time of the influenza virus administration, as compared with other mice. This might be influenced by the events where: when live hPIV2/ΔF is compared with inactivated hPIV2/ΔF, the total amount of proteins secreted into the mouse alveolar lavage is 10 or more times higher for live hPIV2/ΔF; and in vitro hPIV2/ΔF/M2-infected cells exhibit a higher cytopathic effect and higher cytotoxicity than those of hPIV2/ΔF/HN-M2e-infected cells. M2 is a membrane protein composed of 97 amino acid residues. This protein forms a tetramer and works as a proton channel. In the case of the transfer of the full-length M2 protein by live hPIV2/ΔF/M2, the body weights of the mice might be decreased by the action of the functions before influenza infection. On the other hand, inactivated hPIV2/ΔF/HN-M2e caused the expression of a fusion form of M2e with the HN membrane protein. The antigenicity of M2e was enhanced by the fusion with the highly immunogenic HN membrane protein, probably leading to the higher vaccine effect. In fact, the increased antigenicity of M2e fused with *Neisseria meningitidis* outer membrane complex (OMPC) has been reported. The transnasal administration of inactivated hPIV2/ΔF/HN-M2e preferentially induced the IgA antibody against M2e, while its intramuscular administration preferentially induced IgG2 thereagainst.

Live hPIV2/ΔF/HN-M2e was also confirmed to have no vaccine effect on the influenza virus.

The very high vaccine effect exhibited by inactivated hPIV2/ΔF/HN-M2e demonstrated that this inactivated vector system works very effectively as a system for a vaccine against the influenza virus. The possibilities were confirmed that: inactivated hPIV2 that possesses hemagglutinating activity can induce a vaccine effect without the addition of an adjuvant; M2e fused with the viral structural protein functions sufficiently as an antigen for vaccines; the fusion of M2e with the hPIV2 membrane protein can impart a high immune effect to M2e; and toxicity to a recipient is low because the transcription and replication of the viral structural protein are absent.

Example 12 Vaccine Effect of hPIV2/ΔF/HN-Gp-100 on B-16 Melanoma Cell hPIV2/ΔF/HN-gp-100 was examined for its ex vivo preventive tumor inhibitory effect on B-16 melanoma cells.

DC cells were recovered from the femur of mice and cultured in vitro. The vector was added to the DC cells, which were then brought back to the mouse to examine the ex vivo tumor inhibitory effect. As shown in Example 2, the bone marrow was recovered from the femur of a B57BL/6 mouse and cultured (RPMI-1640 medium, 10% FBS) after removal of debris. Every two culture days, the culture solution was replaced with a fresh medium, and GM-CSF (20 ng/mL) and IL-4 (20 ng/mL) were added thereto. The cells cultured for 8 days were examined for their differentiation into DC. The cells were washed and cultured in an RPMI-1640 medium containing 10% FBS. Live hPIV2/ΔF/GFP or hPIV2/ΔF/GFP treated with 0.05% BPL was added at MOI=50 to the culture solution. The cells were cultured for 2 days. The cells were recovered and subcutaneously (SC) administered at a dose of $3\times10^6$ cells to the vicinity of the groin of the 6-week-old B57BL/6 mouse three times at one-week intervals. One week after the final administration, mouse melanoma cells (which were washed with PBS three times before administration) were intradermally (ID) administered at a dose of $5\times10^5$ cells/100 μl to the back of the mouse. After the administration, the tumor axes were measured to calculate a tumor volume. The tumor volume was calculated according to the expression Minor axis of the tumor×Minor axis×Major axis×0.5.

Figure 12:
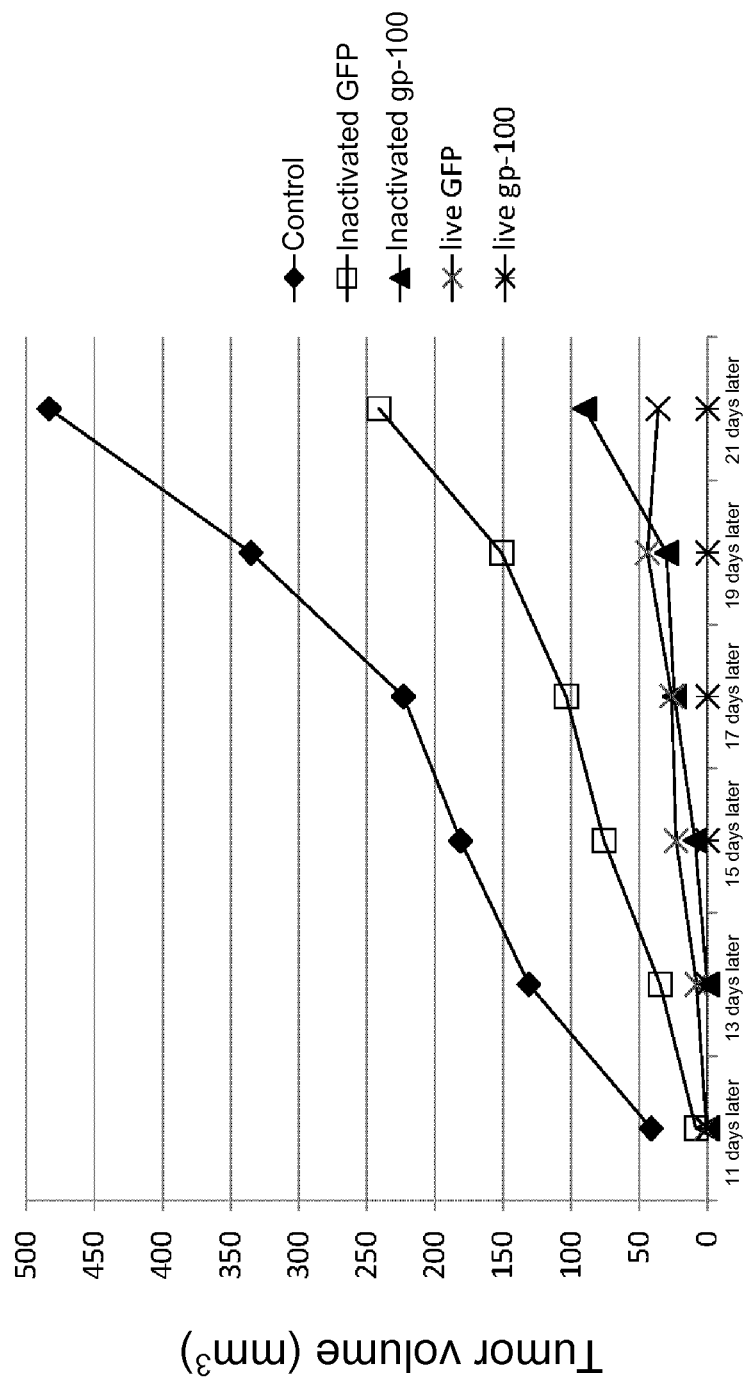
FIG. 12 shows the vaccine effect of hPIV2/ΔF/HN-gp-100 against melanoma cell growth.

The results are shown in FIG. 12. The control group had the largest tumor volume. The live hPIV2/ΔF/HN-gp-100 treatment group produced the highest effect, and tumor growth was not observed in any of the mice during the assay period. Likewise, tumor growth was not observed in some mice in the live hPIV2/ΔF/GFP group. This is presumably because of an effect brought about by the infection by live hPIV2/ΔF/GFP that enhanced the general immune functions of DC.

From these test results, live hPIV2/ΔF/HN-gp-100 was shown to have a higher tumor growth inhibitory effect than that of live hPIV2/ΔF/GFP.

On the other hand, when inactivated hPIV2/ΔF/HN-gp-100 is compared with inactivated hPIV2/ΔF/GFP and the control, inactivated hPIV2/ΔF/HN-gp-100 exhibited an obvious tumor growth inhibitory effect compared with inactivated hPIV2/ΔF/GFP and the control. The tumor inhibitory effect of the inactivated hPIV2 was smaller than that of the live one. This may be because the gene transfer efficiency of hPIV2 is lower for DC than for epithelium-derived cells and infection and gene transfer efficiency is poorer for mouse cells than for human cells. Presumably, the effect of the vector is enhanced with increase in the amount of the vector added.

Live or inactivated hPIV2/ΔF/HN-gp-100 significantly inhibited tumor growth, as compared with live or inactivated hPIV2/ΔF/GFP, suggesting that hPIV2/ΔF/HN-gp-100 allows antigen-presenting cells to present the gp-100 peptide serving as an antigen to induce antitumor immunity such as CTL. In addition, the vector was found to be able to exert its tumor inhibitory effect without the addition of an adjuvant.

Example 13 Vaccine Effects of hPIV2/ΔF/HN-Gp-100 and hPIV2/ΔF/WT-1 on B-16 Melanoma Cell Next, inactivated hPIV2/ΔF/HN-gp-100 and inactivated hPIV2/ΔF/WT-1 (WT-1 sequence used: N terminus-RMP- NAPYL-C terminus (SEQ ID NO: 6)) were examined for their therapeutic effects. The back of a B57BL/6 mouse was shaved, and 2×10⁶ B-16 melanoma cells were intradermally transplanted to the mouse. After 4 days, when the axis of the transplanted B-16 melanoma reached approximately 3 mm, 7.0×10⁶ particles each of inactivated hPIV2/ΔF/HN-gp-100 and inactivated hPIV2/ΔF/WT-1 adjusted to 70 µL were intratumorally administered a total of four times (days 4, 7, 10, and 13 after the cell transplantation). The tumor axes were measured each time. Inactivated hPIV2/ΔF/GFP was administered as a control. The volume of 70 µL was a volume exceeding the tumor volume at the early stage of the administration.

Figure 13:
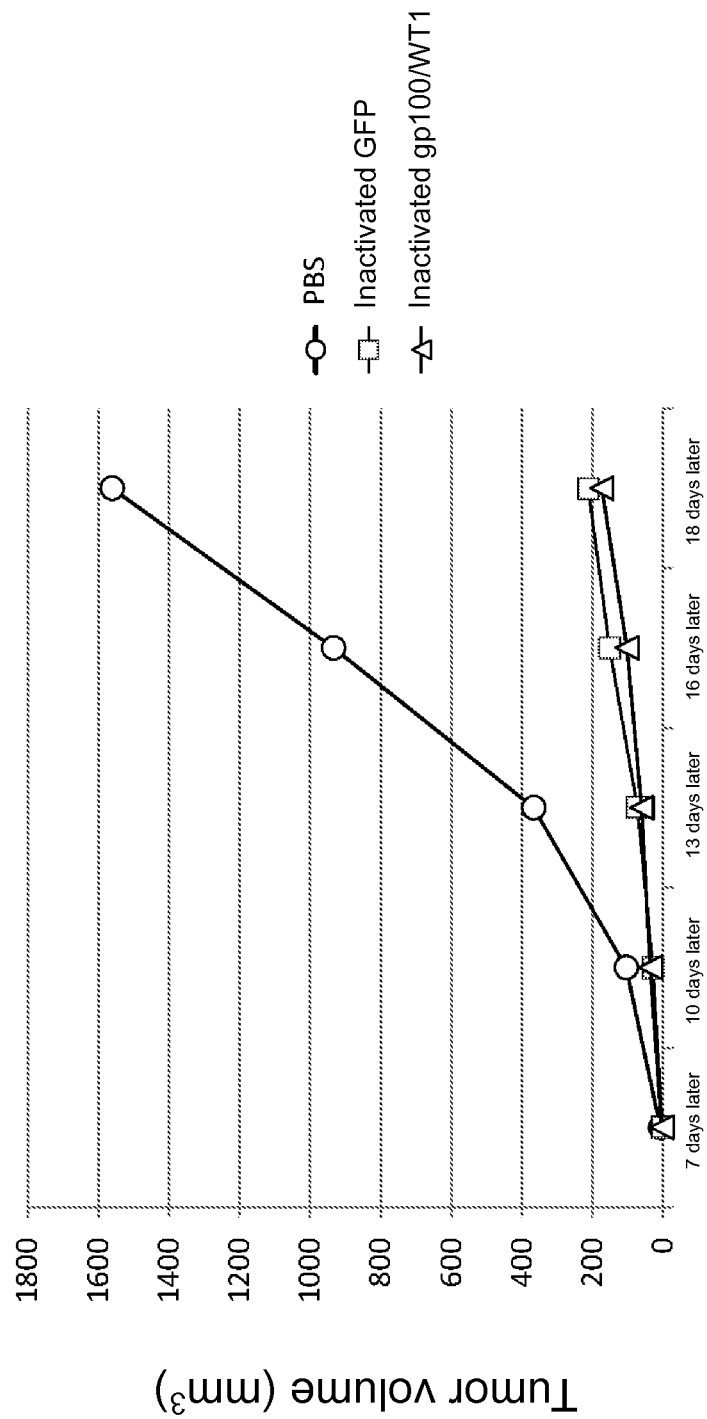
FIG. 13 shows the therapeutic effect of hPIV2/ΔF/HN-gp-100/WT-1 on melanoma cell-transplanted mice.

As a result, in light of the tumor volume, a tumor inhibitory effect was confirmed in the inactivated hPIV2/ΔF/GFP administration group and the inactivated hPIV2/ΔF/HN-gp-100 and inactivated hPIV2/ΔF/WT-1 administration group compared with a PBS administration group (FIG. 13). No large difference was confirmed between the inactivated hPIV2/ΔF/GFP administration group and the inactivated hPIV2/ΔF/HN-gp-100 and inactivated hPIV2/ΔF/WT-1 administration group. In the case of directly administering the vector to tumor, the inhibition of the tumor through the lysis, etc., of the tumor cells by the administration of the vector itself seems to be higher than the tumor inhibitory effect brought about by the induction of immunity. It has been reported that viral components exhibits an antitumor effect by the intratumoral administration of a virus vector harboring no tumor antigen and an inactivated virus vector, suggesting the tumor inhibitory effect brought about by the intratumoral administration of the inactivated vector in this test.

Example 14 Insertion of Foreign Gene to Each Site of hPIV2/ΔF

Two M2e genes (SEQ ID NO: 1) were linked to each other and genes encoding hPIV2 F membrane anchor domain and membrane or intracellular domain proteins were linked on the C-terminal side thereof, i.e., a linkage product of a packaging signal to the vector was constructed. This construct was inserted to hPIV2/ΔF to study whether the foreign gene product was taken up into the vector.

hPIV2 R1, intervening sequence, and R2 were added to the 3' side of the gene construct by the conventional method, and Not I sequences were further located at both ends thereof. The resulting construct was inserted to the Not I site of hPIV2/ΔF to construct a vector plasmid in which two M2e were linked to each other and a fusion protein of the F membrane anchor domain and intramembrane domain proteins was integrated (FIG. 14A). The hPIV2/ΔF carries a Not I restriction site upstream of the NP gene. A foreign gene can be inserted to this site so that the virus can express the foreign gene by itself.

The vector was recovered using F-expressing cells by the conventional method. F-expressing Vero cells (1×10⁶ cells) were infected by a sample recovered from a culture supernatant. The cells thus infected for 8 days were recovered and subjected to Western blot using an anti-M2 antibody.

As a result, as shown in FIG. 14B, anti-M2 antibody-positive reaction was found in the infected cells. This means that the vector carrying the gene of interest was recovered. This vector can be combined with the aforementioned prepared vector to prepare an inactivated vector capable of transferring a larger number of antigens. The extramembrane domain peptide of RSV virus F membrane protein or the extramembrane domain peptide of modified F membrane protein has been transferred by a similar method to construct hPIV2/ΔF.

Vector plasmids having a foreign gene insertion site between NP and P, between P and M, between M and HN, and/or between HN and L in addition to the insertion site upstream of the N gene are constructed in the same way as above. Vector plasmids carrying RSV F protein or RSV modified F protein gene as a transgene are further constructed.

All publications, patents, and patent applications cited herein are incorporated herein by reference in their entirety.

INDUSTRIAL APPLICABILITY

The present invention is useful for a vaccine for prevention or treatment of a disease.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "PMU-9003WO-rev.txt", created Jul. 30, 2015, file size of 4,096 bytes, is hereby incorporated by reference.

The invention claimed is:

1. A virus vector in which a gene encoding an antigenic polypeptide is integrated in a gene of an F protein-defective human parainfluenza virus type 2, wherein the antigenic polypeptide is expressed in the form of a fusion protein with a viral structural protein or a portion thereof, and the virus vector requires that F protein be supplied in trans by a packaging cell in order to produce virus particles having infectious ability, wherein the F protein-defective virus lacks F gene or an extramembrane domain of the F gene.

2. The virus vector according to claim 1, wherein the fusion protein is a fusion protein with any one or more selected from HN protein, F protein, and M protein of the virus, or a portion thereof.

3. The virus vector according to claim 2, wherein the gene encoding an antigenic polypeptide is
   1) located on the 3'-terminal side of the HN gene, wherein the antigenic polypeptide is expressed outside the vector envelope,
   2) located on the 3'-terminal side of the F gene, wherein the antigenic polypeptide is expressed inside the vector envelope, or
   3) located on each of the 3'-terminal side of the HN gene and the 3'-terminal side of the F gene, wherein the antigenic polypeptide is expressed both outside and inside the vector envelope.

4. The virus vector according to claim 1, wherein the antigenic polypeptide is fused with a membrane or intracellular domain of the F or HN membrane protein serving as a viral packaging signal so that the antigenic polypeptide is retained on the vector envelope.

5. The virus vector according to claim 1, wherein the virus has undergone nucleic acid inactivation treatment.

6. The virus vector according to claim 5, wherein the nucleic acid inactivation treatment does not substantially alter the structure of the virus envelope.

7. The virus vector according to claim 1, wherein the antigenic polypeptide is influenza virus M2e protein or a fragment thereof.

8. The virus vector according to claim 1, wherein the antigenic polypeptide is any one or more selected from:
   the group consisting of an antigenic peptide of a virus selected from influenza viruses including a highly virulent influenza virus, parainfluenza virus type 3, RS virus, Hendra virus, SARS virus, Nipah virus, Lassa virus, dengue virus, West Nile virus, human metapneumovirus, Ebola virus, hantavirus, AIDS virus, hepatitis C virus, Lassa virus, human papillomavirus, rubella virus, rotavirus, norovirus, Crimean-Congo hemorrhagic fever virus, herpesvirus, cytomegalovirus, and papillomavirus;
   the group consisting of an antigenic peptide of a bacterium selected from the group A beta-hemolytic *streptococcus, Mycobacterium tuberculosis, Vibrio cholerae*, and *mycoplasma*; and
   the group consisting of cancer antigens gp100, MUC1, NY-ESO-1, MelanA/MART1, TRP2, MAGE, CEA, CAl25, HER2/neu, WT1, and PSA, or fragment(s) thereof.

9. A method for producing a virus vector in which a gene encoding an antigenic polypeptide is integrated in a gene of an F protein-defective human parainfluenza virus type 2, wherein the antigenic polypeptide is expressed in the form of a fusion protein with a viral structural protein or a portion thereof, and the virus vector requires that F protein be supplied in trans by a packaging cell in order to produce virus particles having infectious ability, wherein the F protein-defective virus lacks F gene or an extramembrane domain of the F gene, the method comprising the steps of:
   (1) coculturing:
      (i) a Vero cell transfected with (a) an F gene of human parainfluenza virus type 2 or (b) an F gene of human parainfluenza virus type 2 fused with a gene encoding an antigen, wherein the Vero cell stably expresses the F gene or the F gene fused with the gene encoding the antigen; and
      (ii) an F gene-defective human parainfluenza virus type 2 in which a gene encoding the fusion protein is integrated in a viral gene; and
   (2) isolating virus particles from the culture supernatant;
   wherein the fusion protein is a fusion protein with one or more selected from HN protein, F protein, and M protein of the virus, or a portion thereof.

10. A method for producing a virus vector in which a gene encoding an antigenic polypeptide is integrated in a gene of an F protein-defective human parainfluenza virus type 2, wherein the antigenic polypeptide is expressed in the form of a fusion protein with a viral structural protein or a portion thereof, and the virus vector requires that F protein be supplied in trans by a packaging cell in order to produce virus particles having infectious ability, wherein the F protein-defective virus lacks F gene or an extramembrane domain of the F gene, the method comprising the steps of:
   (1) coculturing:
      (i) a Vero cell transfected with (a) an F gene of human parainfluenza virus type 2 or (b) an F gene of human parainfluenza virus type 2 fused with a gene encoding an antigen, wherein the Vero cell stably expresses the F gene or the F gene fused with the gene encoding the antigen; and
(ii) an F gene-defective human parainfluenza virus type 2 in which a gene encoding the fusion protein is integrated in a viral gene; and
(2) isolating virus particles from the culture supernatant; wherein the fusion protein is a fusion protein with an intracellular domain of the HN protein or the F protein of the virus.

11. A method for producing a virus vector in which a gene encoding an antigenic polypeptide is integrated in a gene of an F protein-defective human parainfluenza virus type 2, wherein the antigenic polypeptide is expressed in the form of a fusion protein with a viral structural protein or a portion thereof, and the virus vector requires that F protein be supplied in trans by a packaging cell in order to produce virus particles having infectious ability, wherein the F protein-defective virus lacks F gene or an extramembrane domain of the F gene, the method comprising the steps of:
(1) coculturing:
(i) a Vero cell transfected with (a) an F gene of human parainfluenza virus type 2 or (b) an F gene of human parainfluenza virus type 2 fused with a gene encoding an antigen, wherein the Vero cell stably expresses the F gene or the F gene fused with the gene encoding the antigen; and
(ii) an F gene-defective human parainfluenza virus type 2 in which a gene encoding the fusion protein is integrated in a viral gene; and
(2) isolating virus particles from the culture supernatant; wherein the antigenic polypeptide is
1) fused on the C-terminal side of the HN protein and expressed outside the vector envelope,
2) fused on the C- or N-terminal side of the F protein and expressed inside the vector envelope, or
3) fused on each of the C-terminal side of the HN protein and the C- or N-terminal side of the F protein or the N-terminal side of the HN protein and expressed both outside and inside the vector envelope.

12. A method for producing a virus vector in which a gene encoding an antigenic polypeptide is integrated in a gene of an F protein-defective human parainfluenza virus type 2, wherein the antigenic polypeptide is expressed in the form of a fusion protein with a viral structural protein or a portion thereof, and the virus vector requires that F protein be supplied in trans by a packaging cell in order to produce virus particles having infectious ability, wherein the F protein-defective virus lacks F gene or an extramembrane domain of the F gene, the method comprising the steps of:
(1) coculturing:
(i) a Vero cell transfected with (a) an F gene of human parainfluenza virus type 2 or (b) an F gene of human parainfluenza virus type 2 fused with a gene encoding an antigen, wherein the Vero cell stably expresses the F gene or the F gene fused with the gene encoding the antigen; and
(ii) an F gene-defective human parainfluenza virus type 2 in which a gene encoding the fusion protein is integrated in a viral gene; and
(2) isolating virus particles from the culture supernatant; wherein the antigenic polypeptide is fused with a membrane or intracellular domain of the HN protein or the F protein of the virus so that the antigenic polypeptide is included on the vector envelope.

13. A method for producing a virus vector in which a gene encoding an antigenic polypeptide is integrated in a gene of an F protein-defective human parainfluenza virus type 2, wherein the antigenic polypeptide is expressed in the form of a fusion protein with a viral structural protein or a portion thereof, and the virus vector requires that F protein be supplied in trans by a packaging cell in order to produce virus particles having infectious ability, wherein the F protein-defective virus lacks F gene or an extramembrane domain of the F gene, the method comprising the steps of:
(1) coculturing:
(i) a Vero cell transfected with (a) an F gene of human parainfluenza virus type 2 or (b) an F gene of human parainfluenza virus type 2 fused with a gene encoding an antigen, wherein the Vero cell stably expresses the F gene or the F gene fused with the gene encoding the antigen; and
(ii) an F gene-defective human parainfluenza virus type 2 in which a gene encoding the fusion protein is integrated in a viral gene; and
(2) isolating virus particles from the culture supernatant; further comprising the step of subjecting the virus to nucleic acid inactivation treatment.

14. The method according to claim 13, wherein the nucleic acid inactivation treatment does not substantially alter the structure of the virus envelope.

15. The method according to claim 9, wherein the antigenic polypeptide is influenza virus M2e protein or a fragment thereof.

16. The method according to claim 9, wherein the antigenic polypeptide is any one or more antigenic peptides selected from:
the group consisting of an antigenic peptide of a virus selected from influenza viruses including a highly virulent influenza virus, parainfluenza virus type 3, RS virus, Hendra virus, SARS virus, Nipah virus, Lassa virus, dengue virus, West Nile virus, human metapneumovirus, Ebola virus, hantavirus, AIDS virus, hepatitis C virus, Lassa virus, human papillomavirus, rubella virus, rotavirus, norovirus, Crimean-Congo hemorrhagic fever virus, herpesvirus, cytomegalovirus, and papillomavirus;
the group consisting of an antigenic peptide of a bacterium selected from the group A beta-hemolytic *streptococcus, Mycobacterium tuberculosis, Vibrio cholerae*, and *mycoplasma*; and
the group consisting of cancer antigens gp100, MUC1, NY-ESO-1, MelanA/MART1, TRP2, MAGE, CEA, CA125, HER2/neu, WT1, and PSA, or fragment(s) thereof.

* * * * *

UNITED STATES PATENT AND TRADEMARK OFFICE
CERTIFICATE OF CORRECTION

PATENT NO. : 9,695,444 B2  
APPLICATION NO. : 14/655417  
DATED : July 4, 2017  
INVENTOR(S) : Masayuki Fukumura et al.

Page 1 of 1

It is certified that error appears in the above-identified patent and that said Letters Patent is hereby corrected as shown below:

In the Specification

Column 6, Line 54, "and up to 10" should read -- and up to $10^7$ --

Column 8, Line 11, "J3-" should read -- β- --

Signed and Sealed this  
Tenth Day of October, 2017

Joseph Matal  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 9

<210> SEQ ID NO 1
<211> LENGTH: 24
<212> TYPE: PRT
<213> ORGANISM: Influenza virus

<400> SEQUENCE: 1

Ser Leu Leu Thr Glu Val Glu Thr Pro Ile Arg Asn Glu Trp Gly Cys
1               5                   10                  15

Arg Cys Asn Asp Ser Ser Asp Asp
            20

<210> SEQ ID NO 2
<211> LENGTH: 9
<212> TYPE: PRT
<213> ORGANISM: Homo sapiens
```

<400> SEQUENCE: 2

Lys Val Pro Arg Asn Gln Asp Trp Leu
1               5

<210> SEQ ID NO 3
<211> LENGTH: 9
<212> TYPE: PRT
<213> ORGANISM: Homo sapiens

<400> SEQUENCE: 3

Ala Leu Leu Pro Ala Val Pro Ser Leu
1               5

<210> SEQ ID NO 4
<211> LENGTH: 9
<212> TYPE: PRT
<213> ORGANISM: Homo sapiens

<400> SEQUENCE: 4

Cys Tyr Thr Trp Asn Gln Met Asn Leu
1               5

<210> SEQ ID NO 5
<211> LENGTH: 9
<212> TYPE: PRT
<213> ORGANISM: Homo sapiens

<400> SEQUENCE: 5

Cys Met Thr Trp Asn Gln Met Asn Leu
1               5

<210> SEQ ID NO 6
<211> LENGTH: 8
<212> TYPE: PRT
<213> ORGANISM: Homo sapiens

<400> SEQUENCE: 6

Arg Met Pro Asn Ala Pro Tyr Leu
1               5

<210> SEQ ID NO 7
<211> LENGTH: 24
<212> TYPE: PRT
<213> ORGANISM: Influenza virus

<400> SEQUENCE: 7

Ser Leu Leu Thr Glu Val Glu Thr Pro Thr Arg Asn Glu Trp Glu Cys
1               5                   10                  15

Arg Cys Ser Asp Ser Ser Asp Asp
            20

<210> SEQ ID NO 8
<211> LENGTH: 24
<212> TYPE: PRT
<213> ORGANISM: Influenza virus

<400> SEQUENCE: 8

Ser Leu Leu Thr Glu Val Glu Thr Leu Thr Arg Asn Gly Trp Gly Cys
1               5                   10                  15

Arg Cys Ser Asp Ser Ser Asp Asp
            20

```
<210> SEQ ID NO 9
<211> LENGTH: 64
<212> TYPE: PRT
<213> ORGANISM: Human parainfluenza virus 2

<400> SEQUENCE: 9

Tyr Ser Leu Ser Ala Ile Ala Leu Ile Leu Ser Val Ile Thr Leu Val
1               5                   10                  15

Val Val Gly Leu Leu Ile Ala Tyr Ile Ile Lys Leu Val Ser Gln Ile
            20                  25                  30

His Gln Phe Arg Ser Leu Ala Ala Thr Thr Met Phe His Arg Glu Asn
        35                  40                  45

Pro Ala Phe Phe Ser Lys Asn Asn His Gly Asn Ile Tyr Gly Ile Ser
    50                  55                  60
```